US008586059B2

(12) United States Patent
Rosenbusch et al.

(10) Patent No.: US 8,586,059 B2
(45) Date of Patent: Nov. 19, 2013

(54) CATTLE VACCINES

(75) Inventors: Ricardo Rosenbusch, Ames, IA (US); Nakhyung Lee, Ames, IA (US)

(73) Assignees: Iowa State University Research Foundation, Inc., Ames, IA (US); Biotechnology Research and Development Corporation, Peoria, IL (US)

( * ) Notice: Subject to any disclaimer, the term of this patent is extended or adjusted under 35 U.S.C. 154(b) by 204 days.

(21) Appl. No.: 13/000,954

(22) PCT Filed: Jun. 3, 2009

(86) PCT No.: PCT/US2009/046135
§ 371 (c)(1),
(2), (4) Date: Dec. 22, 2010

(87) PCT Pub. No.: WO2010/002537
PCT Pub. Date: Jan. 7, 2010

(65) Prior Publication Data
US 2011/0150933 A1 Jun. 23, 2011

Related U.S. Application Data

(60) Provisional application No. 61/078,265, filed on Jul. 3, 2008.

(51) Int. Cl.
*A61K 39/02* (2006.01)
*A61K 49/00* (2006.01)
*A61K 39/09* (2006.01)

(52) U.S. Cl.
USPC ... 424/264.1; 424/9.2; 424/200.1; 424/234.1; 424/9.1

(58) Field of Classification Search
USPC .................. 424/9.1, 9.2, 200.1, 234.1, 264.1
See application file for complete search history.

(56) References Cited

U.S. PATENT DOCUMENTS

| | | | |
|---|---|---|---|
| 2003/0082591 A1 | 5/2003 | Awrey et al. | |
| 2003/0100100 A1* | 5/2003 | Jacobs et al. | 435/252.3 |
| 2003/0147914 A1 | 8/2003 | Keich et al. | |
| 2006/0292135 A1 | 12/2006 | Loomis et al. | |
| 2007/0212727 A1 | 9/2007 | Szalay et al. | |
| 2008/0069842 A9 | 3/2008 | Leonard et al. | |

FOREIGN PATENT DOCUMENTS

WO   WO01/34189   5/2001

OTHER PUBLICATIONS

Chopra-Dewasthaly et al., "First steps towards the genetic manipulation of *Mycoplasma agalactine* and *Mycoplasma bovis* using the transposon Tn4001mod," *Int J Med Microbiol.*, 2005, 294:447-453.

Lee, Nahkyung, "Characterization of an ATP-binding cassette (ABC) transport system involved in nucleoside uptake in *Mycoplasma bovis* strain M23, and discovery of its pathogenicity genes," Iowa State University College of Veterinary Medicine, Jul. 23, 2009.
Lee, Nakhyung, "Characterization of an ABC transport system involved in nucleoside uptake in *Mycoplasma bovis* strain M23, and discovery of its pathogenicity genes." Iowa State University Veterinary Microbiology and Prevenative Medicine, Rosenbusch Lab, May 13, 2009.
Naida J. Osborne, Nakhyung Lee, Ricardo F. Rosenbusch, "Intranasal colonization and Tissue Dissemination of *Mycoplasma bovis* deletion mutant ΔpotABC," Veterinay Summer Scholar Research Program, The College of Veterinary Medicine, Iowa State University, Aug. 12, 2009.
Nakhyung Lee, Daniel Zamzow, Clayton Riedell, Ricardo F. Rosenbusch, "Development of a Transposon Tn4001 Mutant Library of a Pathogenic *Mycoplasma bovis* Strain," 17th Annual Congress of the International Organization for Mycoplasmology, Jul. 4-11, 2008.
Nakhyung Lee, Daniel Zamzow, Ricardo Rosenbusch, "Identification of the Origin of Replication in the Chromosome of *Mycoplasma bovis* and its Use to Construct a Replicative Plasmid." 108th General Meeting of the American Society for Microbiology, Jun. 1-5, 2008.
Ricardo Rosenbusch, Daniel Zamzow, Clayton Riedell, Nakhyung Lee, "Construction of a Random Mutant Library in *Mycoplasma bovis*." 108th General Meeting of the American Society for Microbiology, Jun. 1-5, 2008.
Ricardo Rosenbusch, Nakhyung Lee, Daniel Zamzow, Clayton Riedell, Lee Christensen, "Use of a respiratory Tract Model in Cattle to Screen Transposen Tn4001 Mutants of *Mycoplasma bovis*." 17th Annual Congress of the International Organization for Mycoplasmology, Jul. 4-11, 2008.
Ricardo Rosenbusch, Nakhyung Lee, Lee Christensen, "Identification of *Mycoplasma bovis* Genes Involved in Uptake of Unopsomized Mycoplasmas by Activated Macrophages." 17th Annual Congress of the International Organization for Mycoplasmology, Jul. 4-11, 2008, 133.
Rosenbusch, Ricardo, "Genome analysis in *Mycoplasma bovis*: a window into pathogenicity." International Conference on Bovine Mycoplasmosis, Jul. 9, 2009.
Sirand-Pugnet et al., Being Pathogenic, Plastic, and Sexual while Living with a Nearly Minimal Bacterial genome, *PLOS Genetics*, May 2007, 3:0744-0758.
Song et al., "Functional expression of the Flp recombinase in *Mycobacterium bovis* BCG" *Gene*, 2007, 399:112-119.
Vanden Bush et al., "*Mycoplasma bovis* induces apoptosis of bovine lymphocytes," *FEMS Immunology and Medical Microbiology*, 2002, 32:97-103.
Authorized Officer Lee W. Young, International Search Report and Written Opinion of the International Searching Authority in PCT/US2009/046135, mailed Dec. 3, 2009, 14 pages.
Authorized Officer Athina Nickitas-Etienne, International Preliminary Report on Patentability in PCT/US2009/046135, issued Jan. 5, 2011, 10 pages.

(Continued)

*Primary Examiner* — Rodney P. Swartz
(74) *Attorney, Agent, or Firm* — Fish & Richardson P.C.

(57) ABSTRACT

This document provides live non-pathogenic *M. bovis* bacteria and compositions containing live non-pathogenic *M. bovis* bacteria. This document also provides methods of using live non-pathogenic *M. bovis* bacteria to immunize cattle against infectious diseases (e.g., diseases caused by *M. bovis* bacteria). In addition, methods and materials that can be used to generate live non-pathogenic *M. bovis* bacteria are provided.

32 Claims, 4 Drawing Sheets

(56) References Cited

OTHER PUBLICATIONS

Berthel et al., "Attenuation of Virulence by Distruption of the *Mycobaterium tuberculosis* erp Gene," *Science*, 1998, 282:759-762.
Buddle et al., "Progress in the development of tuberculosis vaccines for cattle and wildfire," *Veterinary Microbiology*, 2006, 112:191-200.
Collins et al., "Generation of Attenuated *Mycobacterium bovis* Strains by Signature-Tagged Mutagenesis for Discovery of Novel Vaccine Candidates," *Infection and Immunity*, 2005, 73(4):2379-2386.
Collins et al., "Vaccine and skin testing properties of two avirulent *Mycobacterium bovis* mutants with and without an additional esat-6 mutation" *Tuberculosis*, 2003, 83:361-366.
Hotter et al., "Transposon Mutagenesis of Mb0100 at the ppel-nrp Locus in *Mycobacerium bovis* Disrupts Phthiocerol Dimycocerostate (PDIM) and Glycosylphenol-PDIM Biosynthesis, Producting an Avirulent Strain with Vaccine Properties at Least Equal to Those of *M. bovis* BCG," *J. of Bacteriology*, 2005, 187(7):2267-2277.
Lee et al., "G-002 Identification of the Origin of Replication in the Chromosome of *Mycoplasma bovis* and Its Use to Construct a Replicative Plasmid," *General Meeting of American Society for Microbiology*, 2008, 1 page (Abstract Only).
Mahairus et al., "Molecular Analysis of Genetic Differences between *Mycobacterium bovis* BCG and Virulent *M. bovis*," *J. of Bacterology*, 1996, 178:1274-1282.
Rosenbusch et al., "G-001, Construction of a Random Mutant Library of *Mycoplasma bovis*," *General Meeting of American Society for Microbiology*, 2008, 1 page (Abstract only).
Wards et al., "An esat6 knockout mutant of *Mycobacterium bovis* produced by homologous recombination will contribute to the development of a live tuberculosis vaccine," *Tubercle and Lung Diseaase*, 2000, 80(4/5):185-189.
European Search Report in International Application No. PCT/US2009/046135, dated Jun. 19, 2012, 11 pages.
New Zealand Office Action in Application No. 589981, dated Apr. 15, 2011, 3 pages.
Chopra-Dewasthaly Rohini et al., "Constructions of the First Shuttle Vectors for Gene Cloning and Homologous Recombination in *Mycoplasma agalactiae*," *FEMS Microbiology Letters*, 253:89-94 (2005), 6 pages.
Cordova, Caio M.M., et al., "Identification of the Origin of Replication of the *Mycoplasma pulmonis* Chromosome and Its Use in ariC Replicative Plasmids," *J. Bacteriol.*, 184(19): 5426-5435 (2002), 11 pages.
European Communication, dated Jul. 17, 2013, 7 pages.
Gates, A.E., et al. "Comparative Assesment of Metabolically Attenuated *Mycoplasma gallisepticum* Mutant as a Live Vaccine for the Prevention of Avian Respiratory Mycoplasmosis," *Vaccine*, 26:2010-2019 (2008) 10 pages.
Hudson, P. et al., Identification of Virulence-Associated Determinant, Dihydrolipoamide Dehydrogenase (*lps*), in *Mycoplasma gallisepticum* through In Vivo Screening of Transposon Mutants, *Infection and Immunity*, 74(2):931-939 (2006), 9 pages.
Janis, C., et al., Versatile Use of *oriC* Plasmids for Functional Genomics of *Mycoplasma capricolum* subsp. *Capricolum, Applied and Exp. Microbio.*, 71(6):2888-2893 (2005), 6 pages \* cited by examiner

SEQ ID NO: 1

TTTTATTAATTATAGAGCAATAATAACCTTATGAATTAAATTAAGCTCATTAA
TAGTCAAACTACATATTAACAATGAACTGTGGATAACTTGTTAGAATACTGTG
GATAACTTGTTATATAAACACTTTATAAACTAACAATATTAATTATTATTTAT
TATTTATATATGAATATCAATAGCACTAATGATAAGGAAATTGCTTTAAAGTC
TTACACTGAAACCTTTTAGATATTCTGAGACAAGAATTAGGCGATCAGATGC
TTTATAAAACTTTTTTGCAAATTTTGAAATCAAAGATATTTCAAAAATAGGC
CACATAACAATTGGAACAACAAACATAACACCTAATTCTCAATATGTGATCA
AAGCTTATGAAAGTAGCATACAAAAATCTCTTGATGAAACATTTGAACGCAA
ATGTACATTTAGCTTTGTTTTACTTGATTCAGCTATAAAAAGAAGATAAAAC
GCGAAAGAAAAGAAGAGGCAATTGAAAATATTGAATTGTCAAATCGTGAAG
TCGACAAAACTAAAACATTTGATAATTATGTAGAAGGCAACTTTAATAAAGA
AGCCATCAGAATAGCAAAATTAATTGTCGATGGTGAAGAAGACTATAATCCA
ATATTTATTTATGGGAAATCCGGAATAGGTAAAACACACTTACTCAACGCCA
TATGTAATGAGTTTCTTAAAAAGATGTTACAGTTAAATACATAAATGCTAAT
TCTTTTACAAGGGATATATCATACTTTCTACAAGAAAATGATCAACGTAAGTT
AAAACAAATAAGAAATCATTTTGACAATGCCGATATCGTTATGTTTGATGACT
TTCAAAGTTACGGAATAGGCAATAAAAAAGCAACCATTGAACTAATTTTTAA
TATTTTAGACAGCAGGATAAACCAAAAAAGAACCACAATAATTTGTTCCGAC
CGGCCTATATATTCATTACAAAATTCATTTGATGCTAGATTGATAAGCCGTCT
TTCAATGGGATTACAACTTTCAATTGATGAACCGCAAAAGCAGACTTGCTG
AAAATATTAGATTATATGATTAACATAAACAAGATGACGCCTGAACTATGAG
AAGACGACGCAAAAATTTTTATTGTTAAGAACCATGCAAACAGTATAAGAAG
TTTAATTGGCGCTATAAATCGTCTAAGGTTCTATAATTCTGAAATTGTTAAAA
CAAATTCAAGATATACGCTTGCCATAGTTAATTCAATTCTTAAAGACATTCAG
CAAGTAAAAGAAAAGTTACGCCAGATGTTATTATTGAATACGTTGCTAAAT
ACTACAAGCTTTCGCGTTCTGAAATACTAGGTAAAGTAGAAGAAAAGATGT
GGTTTTAGCTAGACATATAGCTATTTGAATTGTTAAAAAGCAATTAGACTTAT
CACTGGAACAAATTGGGAAGTTTTTGGCAATAGAGACCACTCTACCATTATT
AATGCTGTTAGAAAAATTGAGAAAGAAACAGAGCAATCTGATAGAACATTTA
AGAGAACTATTTCTGAAATAAGCAACGAGATTTTTAAGAAAAGTTAACATTT
TAAAAAACATTTATAAACATAATGTTTTCTGCAAAAATGCAAAAAAACGATT
AAAAAAACAGCAAAATTAATTCTTTTTATACTTATCAACAAATTAACAAAAC
ATATATTTATTATTTAAGGAAAAAATGAAAATTATTGTAAA

Figure 1

SEQ ID NO: 2 ttaagaaaagttaaCATTTTAAAAAACATTTATAAACATAATGTTTTCTGCAAAAATG
CAAAAAAACGATTAAAAAAACAGCAAAATTAATTCTTTTTATACTTATCAAC
AAATTAACAAAACATATATTTATTATTTAAGGAAAAAtgaaaattattgtaaa

Figure 2

SEQ ID NO: 3

TAGCATTACACTAAAACTTTTTTATTAAATAGTAAAATGTAAATACAATGTGAAATT
GTAATTAATAATTACAATATGGCGCATTGCACATAAAATATTTAAGGACATATT<u>ATG</u>
AGTAAGAAAAAT

Figure 4

CATTLE VACCINES

CROSS-REFERENCE TO RELATED APPLICATIONS

This application is a National Stage application under 35 U.S.C. 371 and claims benefit under 35 U.S.C. 119(a) of International Application No. PCT/US2009/046135, having an International Filing Date of Jun. 3, 2009, which claims priority to U.S. Provisional Application Ser. No. 61/078,265, filed Jul. 3, 2008, the entire contents of which are hereby incorporated by reference.

STATEMENT OF GOVERNMENT SUPPORT

This invention was made with government support under Grant Number 59-3601-3-315_awarded by the United States Department of Agriculture. The government has certain rights in the invention.

BACKGROUND

1. Technical Field

This document relates to methods and materials for protecting cattle from infectious diseases. For example, this document provides compositions having live *Mycoplasma bovis* bacteria and methods of using such compositions to vaccinate cattle against infectious diseases. This document further relates to methods and materials for generating an *M. bovis* bacterium. For example, this document provides vectors for disrupting *M. bovis* genomic sequences and methods of using such vectors to generate an *M. bovis* bacterium.

2. Background Information

*Mycoplasma bovis* can cause multiple types of disease in bovine herds around the world. Such diseases include, for example, mastitis, pneumonia, arthritis, otitis, skin abscesses, infertility, abortion, or combinations thereof. In each form of the disease, mortality can occur. *M. bovis* is thus a significant concern to dairy and beef producers and veterinarians worldwide. A variety of antibiotics have been developed and proposed as tools to mitigate the economic losses and mortality produced by this pathogen. Such antibiotic treatment may only mask *M. bovis* infections temporarily. Furthermore, antibiotic treatment is not effective in preventing *M. bovis* infection of a previously uninfected animal. Vaccines containing inactivated (e.g., killed) *M. bovis* have been developed. However, killed vaccines typically suffer from a variety of drawbacks, including for example, long delays in the initiation of a protective response, marginally reduced clinical disease symptoms, and inability to reduce shedding of a challenge strain. In some cases, killed vaccines can require the use of adjuvants that may not be suitable in certain situations. For example, lactating dairy cows can react to certain adjuvants commonly used in killed vaccines, often leading to a decrease in milk production.

SUMMARY

This document relates to methods and materials for protecting cattle from infectious diseases. For example, this document provides compositions having live *Mycoplasma bovis* bacteria and methods of using such compositions to vaccinate cattle against infectious diseases. This document further relates to methods and materials for generating an *M. bovis* bacterium. For example, this document provides vectors for disrupting *M. bovis* genomic sequences and methods of using such vectors to generate an *M. bovis* bacterium.

This document is based, in part, on the discovery that inoculating cattle with live non-pathogenic *M. bovis* bacteria containing a disruption in one or more nucleic acid sequences results in a protective effect against subsequent *M. bovis* challenge. *M. bovis* is a major cause of disease, mortality, and financial loss in the cattle industry. In certain aspects, this document provides vaccines for protecting cattle against disease and mortality caused by *M. bovis*. For example, this document provides vaccines that contain live non-pathogenic *M. bovis* bacteria, which vaccines generate an immunogenic response, a protective response, or both when administered to cattle. This document also provides methods of using such vaccines to immunize cattle against diseases caused by *M. bovis*. Administration of *M. bovis* vaccines provided herein can improve the health, quality, and disease resistance of cattle which, in turn, can benefit beef and dairy producers and consumers.

In certain aspects, this document provides a live non-pathogenic *M. bovis* bacterium itself, as well as compositions containing such a live non-pathogenic *M. bovis* bacterium. For example, this document provides an *M. bovis* bacterium having disruption(s) in one or more nucleic acid sequences. In certain cases, an *M. bovis* bacterium having disruption(s) in one or more nucleic acid sequences is non-pathogenic as compared to a naturally occurring *M. bovis* bacterium lacking such disruption(s).

Additionally, this document provides methods and materials that can be used to generate a live non-pathogenic *M. bovis* bacterium. For example, this document provides vectors containing an origin of replication that functions in *M. bovis*. Additionally, this document provides a multi-step strategy for generating an *M. bovis* bacterium that includes a disruption in one or more nucleic acid sequences.

In general, one aspect of this document features an immunogenic composition comprising a pharmaceutically acceptable carrier and a live *M. bovis* bacterium comprising a disruption present in at least one nucleic acid sequence. A live *M. bovis* bacterium containing such a disruption can be non-pathogenic as compared to a reference *M. bovis* bacterium containing the at least one nucleic acid sequence and lacking the disruption. A disruption can be an insertion, e.g., between about 18 and 5500 nucleotides. A disruption can be a deletion, e.g., between about 2000 and 4000 nucleotides. The at least one nucleic acid sequence can be a nucleic acid sequence listed in Table 1 (e.g., a nucleic acid sequence that encodes a p59 polypeptide) or nucleic acid sequence that controls expression of a nucleic acid sequence listed in Table 1 (e.g., a nucleic acid sequence that controls expression of a p59 polypeptide). A reference *M. bovis* strain can be strain M23. Administration of such a composition to a bovine animal can induce a protective response against *M. bovis* (e.g., a pathogenic *M. bovis* strain).

In another aspect, this document features an immunogenic composition comprising live *M. bovis* bacterium having a first disruption present in a first nucleic acid sequence and a second disruption present in a second nucleic acid sequence. A live *M. bovis* bacterium containing such a disruption can be non-pathogenic as compared to a reference *M. bovis* bacterium containing said first and second nucleic acid sequences and lacking said first and second disruptions. A first nucleic acid sequence can be a nucleic acid sequence listed in Table 1 (e.g., a nucleic acid sequence that encodes a p59 polypeptide) or a polypeptide that controls expression of a nucleic acid sequence listed in Table 1 (e.g., a nucleic acid sequence that controls expression of a p59 polypeptide). A second nucleic acid sequence can be a nucleic acid sequence listed in Table 2 (e.g., a nucleic acid sequence that encodes a potC or hemK polypeptide) or a polypeptide that controls expression of a nucleic acid sequence listed in Table 2 (e.g., a nucleic acid sequence that controls expression of a potC or hemK polypeptide). A reference M. bovis strain can be strain M23. Such a live M. bovis bacterium can lack an exogenous nucleic acid sequence encoding a polypeptide having antibiotic resistance activity, a Tn4001 transposon, or both. Administration of such a composition to a bovine animal can induce a protective response against M. bovis (e.g., a pathogenic M. bovis strain).

In another aspect, this document features methods of reducing M. bovis colonization (e.g., colonization of bronchial lymph nodes, lower tracheal mucosa, upper tracheal mucosa, tonsils, nasal mucosa, mammary glands, and combinations thereof) in a bovine animal exposed to pathogenic M. bovis bacteria. In another aspect, this document features methods of reducing the number or severity of lung lesions, mortality, or both in a bovine animal exposed to pathogenic M. bovis bacteria.

In another aspect, this document provides methods of generating a live M. bovis bacterium comprising disrupting a first and second nucleic sequence. A live M. bovis bacterium generated by methods provided herein containing such first and second disruptions can be non-pathogenic as compared to a reference M. bovis bacterium containing the first and second nucleic acid sequences and lacking the disruptions. A first nucleic acid sequence can be a nucleic acid sequence listed in Table 1 (e.g., a nucleic acid sequence that encodes a p59 polypeptide) or a polypeptide that controls expression of a nucleic acid sequence listed in Table 1 (e.g., a nucleic acid sequence that controls expression of a p59 polypeptide). A second nucleic acid sequence can be a nucleic acid sequence listed in Table 2 (e.g., a nucleic acid sequence that encodes a potC or hemK polypeptide) or a polypeptide that controls expression of a nucleic acid sequence listed in Table 2 (e.g., a nucleic acid sequence that controls expression of a potC or hemK polypeptide). Nucleic acid sequences can be disrupted by inserting a nucleic acid insert such as, for example, a transposon. A nucleic acid insert can comprise an excision sequence (e.g., FRT sites) that can be excised upon exposure to an appropriate agent (e.g., FLP recombinase). Such a live M. bovis bacterium can lack an exogenous nucleic acid sequence encoding a polypeptide having antibiotic resistance activity, a Tn4001 transposon, or both.

In another aspect, this document provides isolated nucleic acids comprising a sequence selected from the group consisting of: SEQ ID NO: 1, a sequence that is at least 90% identical to SEQ ID NO: 1, SEQ ID NO: 2, and a sequence that is at least 90% identical to SEQ ID NO: 2. In another aspect, this document provides vectors comprising such sequences.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

FIG. 1: Nucleic acid sequence of a region (SEQ ID NO: 1) of the M. bovis genome containing an oriC origin of replication.

FIG. 2: Nucleic acid sequence of a region (SEQ ID NO: 2) of the M. bovis genome containing an oriC origin of replication.

FIG. 4: M. bovis p81 promoter and nucleic acid sequence encoding the first five amino acids of the p81 polypeptide (SEQ ID NO: 3). The ATG start codon is underlined.

DETAILED DESCRIPTION

Figure 3:
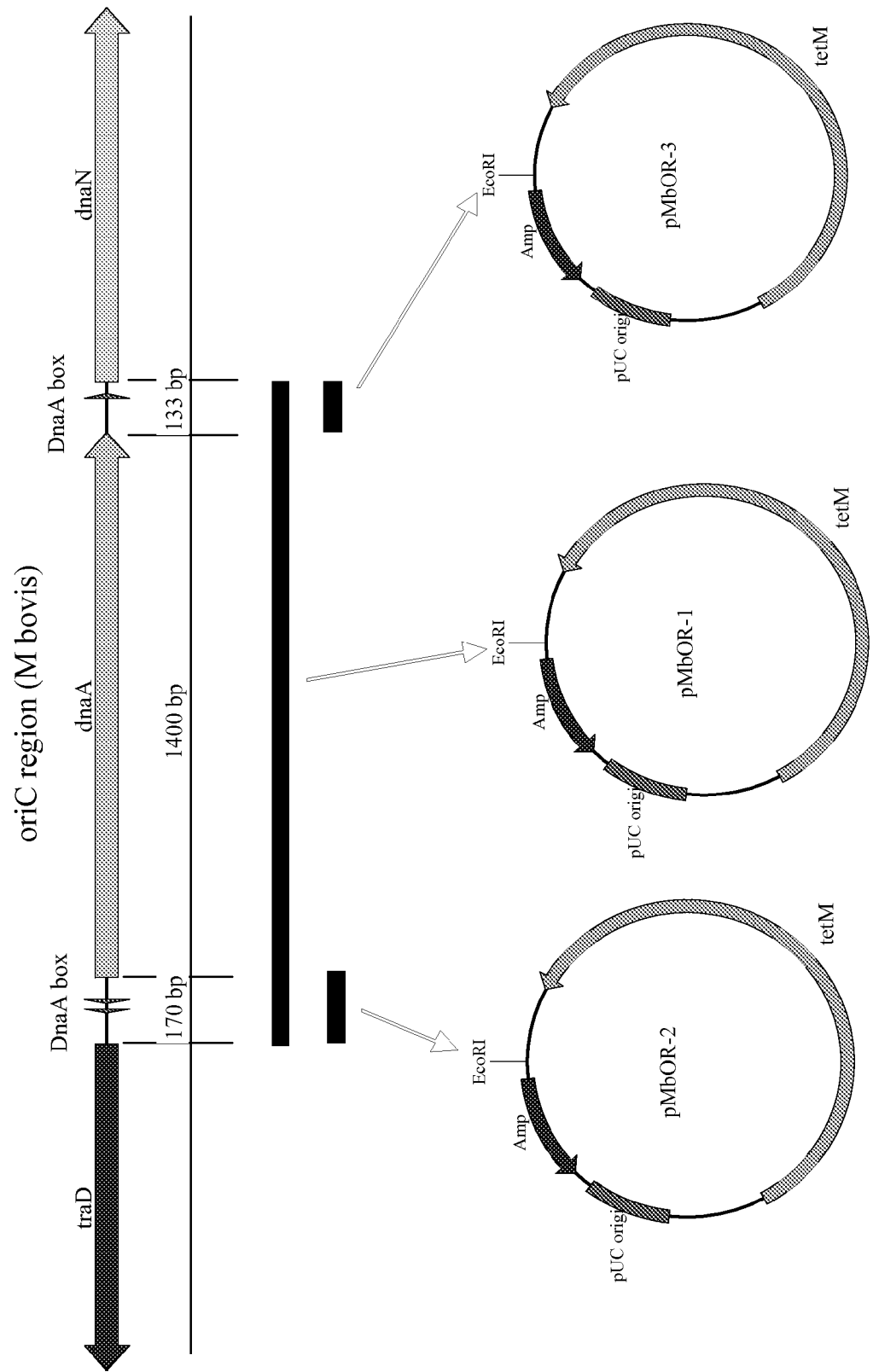
FIG. 3: oriC region of the M. bovis genome and constructs pMbOR-1, pMbOR-2, and pMbOR-3.

This document relates to methods and materials for protecting cattle from infectious diseases. For example, this document provides compositions having live Mycoplasma bovis bacteria and methods of using such compositions to vaccinate cattle against infectious diseases. This document further relates to methods and materials for generating an M. bovis bacterium. For example, this document provides vectors for disrupting M. bovis genomic sequences and methods of using such vectors to generate an M. bovis bacterium.

This document provides M. bovis bacteria having a disruption in one or more nucleic acid sequences as compared to nucleic acid sequence(s) present in a reference M. bovis strain (e.g., M. bovis strain M23 or M. bovis strain PG45 (ATCC 25523)). In some cases, an M. bovis bacterium can include a disruption in one or more nucleic acid sequences as compared to a nucleic acid sequence(s) present in a naturally occurring M. bovis strain. In some cases, an M. bovis bacterium can include a disruption in one or more nucleic acid sequences as compared to a nucleic acid sequence(s) present in a non-naturally occurring M. bovis strain (e.g., a strain that has been previously mutated or attenuated). A reference M. bovis strain, whether naturally or non-naturally occurring, can be pathogenic or non-pathogenic.

The term "disruption" as used herein refers to any change in a nucleic acid sequence (e.g., of an M. bovis bacterium) as compared to a reference nucleic acid sequence (e.g., a nucleic acid sequence present in a naturally or non-naturally occurring M. bovis bacterium). For example, a disruption can include one or more nucleic acid insertions (e.g., transposition events and single amino acid insertions), deletions, substitutions, or combinations thereof as compared a naturally or non-naturally occurring M. bovis strain.

A nucleic acid insertion can include the insertion of up to 10, up to 20, up to 30, up to 40, up to 50, up to 60, up to 70, up to 80, up to 90, up to 100, up to 150, up to 200, up to 250, up to 300, up to 350, up to 400, up to 450, up to 500, up to 600, up to 700, up to 800, up to 900, up to 1000, up to 1100, up to 1200, up to 1300, up to 1400, up to 1500, up to 1600, up to 1700, up to 1800, up to 1900, up to 2000, up to 2100, up to 2200, up to 2300, up to 2400, up to 2500, up to 2600, up to 2700, up to 2800, up to 2900, up to 3000, up to 3100, up to 3200, or more nucleotides as compared to a reference nucleic acid sequence. In some cases, an insertion can include the insertion of between 18 and 5500 nucleotides. In some cases, a nucleic acid insertion can inactivate or decrease the expression of a polypeptide encoded by a nucleic acid sequence containing the insertion. In some cases, a nucleic acid insertion can inactivate or decrease the expression of a polypeptide encoded by a nucleic acid sequence that is regulated by a nucleic acid sequence containing the insertion (e.g., the nucleic acid sequence containing an insertion can encode a transcription factor or other polypeptide involved in expression of the polypeptide). Any nucleic acid sequence can be inserted. Exemplary nucleic acid sequences that can be inserted include, without limitation, transposons (e.g., Tn4001, Tn4001mod, pRIT), nucleic acid sequences encoding a marker polypeptide (e.g., a polypeptide that provides antibiotic resistance or nucleic acid sequences that encode a marker such as lacZ), non-coding nucleic acid sequences, and combinations thereof. In some cases, inserted nucleic acid sequences can include sequences that are present in a naturally occurring or non-naturally occurring organism (e.g., a transgenic organism). In some cases, inserted nucleic acid sequences can include sequences from vectors (e.g., bacterial, mammalian, or insect vectors) such as plasmids, cosmids, phagemids, BACs, and combinations thereof. In some cases, inserted nucleic acid sequences can include sequences that do not occur in any organism or vector. For example, inserted nucleic acid sequences can be chemically synthesized.

A nucleic acid deletion can include the deletion of up to 10, up to 20, up to 30, up to 40, up to 50, up to 60, up to 70, up to 80, up to 90, up to 100, up to 150, up to 200, up to 250, up to 300, up to 350, up to 400, up to 450, up to 500, up to 600, up to 700, up to 800, up to 900, up to 1000, up to 1100, up to 1200, up to 1300, up to 1400, up to 1500, up to 1600, up to 1700, up to 1800, up to 1900, up to 2000, up to 2100, up to 2200, up to 2300, up to 2400, up to 2500, up to 2600, up to 2700, up to 2800, up to 2900, up to 3000, or more nucleotides as compared to a reference nucleic acid sequence. In some cases, a deletion can include a deletion of between 2000 and 4000 nucleotides. In some cases, a nucleic acid deletion can inactivate or decrease the expression of a polypeptide encoded by a nucleic acid sequence containing the deletion. In some cases, a nucleic acid deletion can inactivate or decrease the expression of a polypeptide encoded by a nucleic acid sequence that is regulated by a nucleic acid sequence containing the deletion (e.g., the nucleic acid sequence containing a deletion can encode a transcription factor or other polypeptide involved in expression of the polypeptide).

A nucleic acid substitution can include a substitution of 1, 2, 3, 4, 5, 6, 7, 8, 9, 10, 20, 30, 40, 50, 60, 70, 80, 90, or more nucleotides as compared to a reference nucleic acid sequence. In some cases, a nucleic acid substitution can inactivate or decrease the expression of a polypeptide encoded by a nucleic acid sequence containing the substitution. In some cases, a nucleic acid substitution can inactivate or decrease the expression of a polypeptide encoded by a nucleic acid sequence that is regulated by a nucleic acid sequence containing the substitution (e.g., the nucleic acid sequence containing a substitution can encode a transcription factor or other polypeptide involved in expression of the polypeptide).

Any of a variety of disruptions can be engineered into an *M. bovis* nucleic acid sequence. Examples of nucleic acid sequences that can be disrupted include, without limitation, nucleic acid sequences that encode a polypeptide, nucleic acid sequences that affect expression of a polypeptide, nucleic acid sequences that affect the rate of production or stability of an mRNA or a polypeptide (e.g., transcription elements, sequences in the untranslated regions of an mRNA, introns, and combinations thereof), nucleic acid sequences that encode RNAs (e.g., mRNAs, tRNAs, rRNAs), and combinations thereof.

In some cases, an *M. bovis* bacterium can contain two or more nucleic acid sequence disruptions. In some cases, two or more nucleic acid disruptions can be in the same nucleic acid sequence (e.g., a nucleic acid sequence that encodes a polypeptide such as, without limitation, a nucleic acid sequence encoding a p59 polypeptide). In some cases, two or more nucleic acid disruptions can be in different nucleic acid sequences (e.g., in nucleic acid sequences that encode different polypeptides). In some cases, nucleic acid sequence disruptions can be of the same type. For example, an *M. bovis* bacterium can contain a first insertion in a first nucleic acid sequence, and a second insertion in a second nucleic acid sequence. The first and second insertions can have the same sequence, either partially or in whole, or can have different sequences. In some cases, nucleic acid sequence disruptions can be of different types. For example, an *M. bovis* bacterium can contain an insertion in a first nucleic acid sequence, and a deletion in a second nucleic acid sequence.

*M. bovis* nucleic acid sequences can be disrupted by any of a variety of techniques. For example, nucleic acid sequences can be disrupted by using transposons to insert nucleic acid sequences into the *M. bovis* genome. Transposons can insert themselves randomly into a target nucleic acid sequence, without discriminating on the basis of sequence. Transposons can be provided as part of a larger nucleic acid construct, such as a vector. For example, the Tn40001mod vector contains a transposon sequence that is capable of inserting itself into the *M. bovis* genome (see e.g., Chopra-Dewasthaly et al., Int J Med Microbiol., 294(7), 447-53, (2005)), as well as resistance markers for ampicillin, gentamycin, and tetracycline, and a multi-cloning site for inserting a nucleic acid sequence of interest. In some cases, the insertion of a transposon can occur in a reversible manner through transposase mediated excision. Transposase mediated excision transposon can restore a nucleic acid sequence to its original sequence prior to transposition. In some cases, transposase mediated excision transposon can leave one or more nucleotide residues behind, resulting in an altered target nucleic acid sequence. In some cases, transposase mediated excision transposon can result in an altered target nucleic acid sequence that is missing one or more nucleotide residues (e.g., resulting from faulty repair of the sequence after transposon excision). In some cases, a nucleic acid sequence can be disrupted by using transposon that is defective in its ability to reversibly excise itself, permanently disrupting the target nucleic acid sequence of interest.

In some cases, disruption of a nucleic acid sequence of interest can be obtained using a vector that is able to persist in *M. bovis* for an extended period of time after transformation. The longer a transformed vector is maintained in *M. bovis*, the greater the likelihood of successful disruption (e.g., by transposition into or recombination with a nucleic acid sequence of interest). In some cases, disruption of a nucleic acid sequence of interest can be obtained using a vector that contains an origin of replication that functions in *M. bovis*, which vector can persist in *M. bovis* longer than a vector that lacks such an origin of replication.

This document provides vectors containing an origin of replication that functions in *M. bovis*, and methods of using such vectors to disrupt nucleic acid sequences. In some cases, an origin of replication can be the oriC region of the *M. bovis* genome, or a fragment thereof. The oriC region can include a ~1.7 kb region (SEQ ID NO: 1, FIG. 1) of the *M. bovis* genome containing clusters of DnaA binding boxes located in a region about 170 nucleotides upstream of the *M. bovis* dnaA gene, and located in a region about 133 nucleotides downstream of the *M. bovis* dnaA gene.

In some cases, a vector for disrupting nucleic acid sequences in *M. bovis* can include the nucleic acid sequence of SEQ ID NO: 1. In some cases, a vector for disrupting nucleic acid sequences in *M. bovis* can include a sequence homologous to SEQ ID NO: 1. For example, such vectors can include a sequence having 70%, 75%, 80%, 85%, 90%, 91%, 92%, 93%, 94%, 95%, 96% 97%, 98%, 99% or higher sequence identity to SEQ ID NO: 1, which sequence functions as an origin of replication in *M. bovis*.

In some cases, a vector for disrupting nucleic acid sequences in *M. bovis* can include a fragment of the nucleic acid sequence of SEQ ID NO: 1. For example, such a vector can include a sequence that includes 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, or more nucleotides of SEQ ID NO: 1, which sequence functions as an origin of replication in *M. bovis*. In some cases, a vector for disrupting nucleic acid sequences in *M. bovis* can include a sequence homologous to a fragment of the nucleic acid sequence of SEQ ID NO: 1. For example, such a vector can include a sequence having 70%, 75%, 80%, 85%, 90%, 91%, 92%, 93%, 94%, 95%, 96% 97%, 98%, 99% or higher sequence identity to a sequence that includes 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, or more nucleotides of SEQ ID NO: 1, which sequence functions as an origin of replication in M. bovis.

In some cases, a vector for disrupting nucleic acid sequences in M. bovis can include the nucleic acid sequence of SEQ ID NO: 2 (FIG. 2). In some cases, a vector for disrupting nucleic acid sequences in M. bovis can include a sequence homologous to SEQ ID NO: 2. For example, such vectors can include a sequence having 70%, 75%, 80%, 85%, 90%, 91%, 92%, 93%, 94%, 95%, 96% 97%, 98%, 99% or higher sequence identity to SEQ ID NO: 2, which sequence functions as an origin of replication in M. bovis.

In some cases, a vector for disrupting nucleic acid sequences in M. bovis can include a fragment of the nucleic acid sequence of SEQ ID NO: 2. For example, such a vector can include a sequence that includes 10, 15, 20, 25, 30, 35, 40, 45, 50, 55, 60, 65, 70, 75, 80, 85, 90, 95, 100, 105, 110, 115, 120, 125, 130, or more nucleotides of SEQ ID NO: 2, which sequence functions as an origin of replication in M. bovis. In some cases, a vector for disrupting nucleic acid sequences in M. bovis can include a sequence homologous to a fragment of the nucleic acid sequence of SEQ ID NO: 2. For example, such a vector can include a sequence having 70%, 75%, 80%, 85%, 90%, 91%, 92%, 93%, 94%, 95%, 96% 97%, 98%, 99% or higher sequence identity to a sequence that includes 0, 15, 20, 25, 30, 35, 40, 45, 50, 55, 60, 65, 70, 75, 80, 85, 90, 95, 100, 105, 110, 115, 120, 125, 130, or more nucleotides of SEQ ID NO: 2, which sequence functions as an origin of replication in M. bovis.

Disrupting nucleic acid sequences using vectors that include an origin of replication that functions in M. bovis can result in greater disruption efficiency (e.g., by transposition into or recombination with a nucleic acid sequence of interest). Greater disruption efficiency can be achieved using vectors containing such an origin of replication in combination with one or more selection markers such as an antibiotic resistance marker. For example, a vector containing an origin of replication and an antibiotic resistance marker, when grown under selection pressure, can persist in M. bovis longer than a vector lacking either or both of the origin of replication and an antibiotic resistance marker, thus increasing the likelihood of a successful disruption event.

In some cases, a non-pathogenic M. bovis bacterium can contain a disruption in one or more nucleic acid sequences as compared to a reference pathogenic strain of M. bovis (e.g., M. bovis strain M23 or M. bovis strain PG45 (ATCC 25523)), which disruptions result in non-pathogenicity of the M. bovis bacterium. The term "non-pathogenic" as used herein refers to the property of having a reduced ability to cause disease, the property of causing a less severe form of the disease (e.g., reduced clinical symptoms, reduced time course for the disease, or both), and combinations thereof. For example, nucleic acid sequence disruptions can lead to a complete lack of clinical symptoms, a reduction in the severity of clinical symptoms, a reduction in the length of time symptoms persist in individuals, a reduction or complete lack of spread of the disease amongst individuals, or any of a variety of other criteria used to assess the degree of pathogenicity. In some cases, a non-pathogenic bacterium does not cause disease at all.

When used in comparison to a reference bacterium (e.g., a pathogenic bacterium), the term "non-pathogenic" refers to the property of having a reduced ability to cause disease, the property of causing a less severe form of the disease as compared to the reference bacterium, or both. In general, bacteria and other infectious agents can exhibit a spectrum of pathogenicity ranging from completely non-pathogenic (e.g., no disease symptoms or other adverse effects) to highly pathogenic (e.g., causing the most severe symptoms of a disease such as death or causing disease symptoms that persist for the longest period of time). An M. bovis bacterium provided herein that contains a disruption in one or more nucleic acid sequences as compared to a reference strain of M. bovis can be "non-pathogenic" as compared to the reference strain, even though the reference strain itself is less pathogenic than another M. bovis strain.

In some cases, an animal infected with a non-pathogenic bacterium provided herein can exhibit clinical symptoms that are reduced in severity by 50%, 60%, 70%, 80%, 90%, 95%, 96%, 97%, 98%, 99% or 100% (e.g., as determined by standard quantitative measures appropriate for the disease of interest) as compared to the clinical symptoms exhibited by an animal infected with a reference bacterium. Examples of clinical symptoms that can be reduced in severity upon infection with a non-pathogenic M. bovis bacterium provided herein include, without limitation, fever, coughing, rapid or labored breathing, inflammation (e.g., of the udders), swelling of the joints, and combinations thereof. In some cases, an animal infected with a non-pathogenic bacterium provided herein can exhibit clinical symptoms that are reduced in severity to such an extent that the animal lives after being infected, while an animal infected with a reference bacterium exhibits clinical symptoms of such severity as to result in death. In some cases, an animal infected with a non-pathogenic bacterium can exhibit clinical symptoms that are reduced in duration by 50%, 60%, 70%, 80%, 90%, 95%, 96%, 97%, 98%, 99% or 100% as compared to the clinical symptoms exhibited by an animal infected with a reference bacterium.

In some cases, a non-pathogenic strain of M. bovis can be generated by disrupting at least one nucleic acid sequence of a pathogenic strain of M. bovis, whether such a pathogenic strain is naturally or non-naturally occurring. Pathogenic strains include, without limitation, strains M23, 428E, DSA16, and Cs499.

In some cases, a non-pathogenic strain of M. bovis can be generated by disrupting at least one nucleic acid sequence of a non-pathogenic strain of M. bovis, whether such a non-pathogenic strain is naturally or non-naturally occurring. Non-pathogenic strains include, without limitation, strains M31 and M45.

This document provides non-pathogenic M. bovis strains that can include a disruption in one or more nucleic acid sequences. Examples of M. bovis nucleic acid sequences that can be disrupted include, without limitation, nucleic acid sequences listed in Table 1. In some cases, a nucleic acid sequence (including, without limitation, a nucleic acid sequence listed in Table 1) present in a reference M. bovis strain can be disrupted to result in an M. bovis strain that is non-pathogenic as compared to the reference M. bovis strain lacking the disruption. Different M. bovis strains may contain nucleic acid sequences that are homologous to the nucleic acid sequences listed in Table 1, but that differ in sequence from one another. For example, such homologs can differ by one or more nucleotides, and yet still be recognized from sequence identity (e.g., as determined by a program such as DNAMAN or Blast) as homologs. Such homologs present in different M. bovis strains can be disrupted by any of the methods provided herein.

TABLE 1

Examples of *M. bovis* nucleic acid sequences that can be disrupted.

| Gene Name | Gene product | *M. agalactiae* ortholog | *M. agalactiae* Accession No. | *M. agalactiae* Gene No. |
|---|---|---|---|---|
| p59 | ABC transporter ATP-binding protein A | MAG 0140 | CU 179680 | gi 148291314 |
|  | Sugar ABC transporter permease B | MAG 0150 | CU 179680 | gi 148291314 |
|  | Sugar ABC transporter, permease C | MAG 0160 | CU 179680 | gi 148291314 |
| p48 | Potential sugar ABC transporter | MAG 0120 | CU 179680 | gi 148291314 |
| lpoA | Lipoate protein ligase | MAG 0600 | CU 179680 | gi 148291314 |
| oppA | Oligopeptide permease A | MAG 1000 | CU 179680 | gi 148291314 |
| oppB | Oligopeptide permease B | MAG 1010 | CU 179680 | gi 148291314 |
| oppC | Oligopeptide permease C | MAG 1020 | CU 179680 | gi 148291314 |
| oppD | Oligopeptide permease D | MAG 1030 | CU 179680 | gi 148291314 |
| deoB | Phosphopentomutase | MAG 2800 | CU 179680 | gi 148291314 |
| pepO | Endopeptidase O | MAG 3680 | CU 179680 | Gi 148291314 |

In some cases, a nucleic acid sequence to be disrupted can encode or control expression of a polypeptide. For example, the p59 nucleic acid sequence can encode a p59 polypeptide. In some cases, a polypeptide can exhibit one or more functions in *M. bovis*, which functions can provide the basis for identifying other nucleic acid sequences that can be disrupted. For example, a p59 polypeptide can suppress lymphocytes in vitro. In some cases, in vitro lymphocyte suppression assays can be used to identify other *M. bovis* nucleic acid sequences that can be disrupted, which nucleic acid sequences can encode or control expression of a polypeptide that affects lymphocyte suppression.

In some cases, this document provides non-pathogenic *M. bovis* strains that can include a disruption in one or more nucleic acid sequences listed in Table 2. In some cases, a nucleic acid sequence (including, without limitation, a nucleic acid sequence listed in Table 2) present in a reference *M. bovis* strain can be disrupted to result in an *M. bovis* strain that is non-pathogenic as compared to the reference *M. bovis* strain lacking the disruption. In some cases, a nucleic acid sequence (including, without limitation, a nucleic acid sequence listed in Table 2) present in a reference *M. bovis* strain can be disrupted to result in an *M. bovis* strain that exhibits a level of pathogenicity that is similar to that exhibited by the reference *M. bovis* strain lacking the disruption.

Different *M. bovis* strains may contain nucleic acid sequences that are homologous to the nucleic acid sequences listed in Table 2, but that differ in sequence from one another. For example, such homologs can differ by one or more nucleotides, and yet still be recognized from sequence identity (e.g., as determined by a program such as DNAMAN or Blast) as homologs. Such homologs present in different *M. bovis* strains can be disrupted by any of the methods provided herein.

TABLE 2

Examples of *M. bovis* nucleic acid sequences that can be disrupted.

| Gene Name | Gene product | *M. agalactiae* ortholog | *M. agalactiae* Accession No. | *M. agalactiae* Gene No. |
|---|---|---|---|---|
| hemK | DAM methylase | MAG 2070 | CU 179680 | gi 148291314 |
| potC | spermidine/putrescine tranporter C | MAG 1270 | CU 179680 | gi 148291314 |
| oppF | oligopeptide permease F | MAG 1040 | CU 179680 | gi 148291314 |
| deoA | thymidine phosphorilase | MAG 5120 | CU 179680 | gi 148291314 |

In some cases, a nucleic acid sequence to be disrupted can encode or control expression of a polypeptide. For example, a potC nucleic acid sequence can encode a potC polypeptide. In some cases, a polypeptide can exhibit one or more functions in *M. bovis*, which functions can provide the basis for identifying other nucleic acid sequences that can be disrupted. For example, a potC polypeptide can affect colonization of *M. bovis*. In some cases, colonization assays can be used to identify other *M. bovis* nucleic acid sequences that can be disrupted, which nucleic acid sequences can encode or control expression of a polypeptide that affects colonization.

This document also provides non-pathogenic *M. bovis* strains that can include a disruption in two or more nucleic acid sequences. For example, a non-pathogenic *M. bovis* strain can include a disruption in a first nucleic acid sequence listed in Table 1 and a second nucleic acid sequence listed in Table 2. In some cases, non-pathogenic strains provided herein can contain disruptions in two or more nucleic acid sequences that encode or control expression of polypeptides that affect two different aspects of *M. bovis* pathogenesis. For example, non-pathogenic *M. bovis* strains provided herein can contain a first disruption in a nucleic acid sequence encoding or controlling expression of a polypeptide that affects lymphocyte suppression, and a second disruption in a nucleic acid sequence that encodes or controls expression of a polypeptide that affects colonization.

This document also provides materials and methods for immunizing cattle against *M. bovis*. For example, non-pathogenic *M. bovis* bacteria provided herein can be used in vaccines for immunizing cattle against infectious disease caused by pathogenic *M. bovis*. This document also provides immunogenic compositions containing such non-pathogenic *M. bovis* bacteria, which immunogenic compositions can also be used as vaccines. The term "immunogenic", as used herein, refers to the characteristic of eliciting an immune response in an animal (e.g., a bovine animal). Thus, the term "immunogenic composition" as used herein refers to a composition that, upon administration to an animal, results in an immune response in that animal against one or more components of the immunogenic composition. In some cases, an immune response can be measured by "seroconversion", or the development of detectable specific antibodies to an immunogenic agent (e.g., *M. bovis*) in the blood serum as a result of immunization. Standard serological techniques (e.g., immunoassays, ELISAs) can be used to test for antibodies resulting from seroconversion.

In some cases, an immune response induced by exposure to an immunogenic composition provided herein can protect an animal against one or more pathogens that are not present in the immunogenic composition. For example, immunogenic compositions provided herein that include one or more non-pathogenic *M. bovis* strains that have a disruption in one or more nucleic acid sequences can provide protection against a naturally or non-naturally occurring pathogenic *M. bovis* strain, which pathogenic *M. bovis* strain lacks such disruptions and is not present in the immunogenic composition. In some cases, immunization with a non-pathogenic *M. bovis* strain can provide an immune response against a pathogenic *M. bovis* strain when the non-pathogenic and pathogenic strains share sufficient structural similarities such that one or more epitopes of the non-pathogenic strain generates an immune response against one or more similar or identical epitopes of the pathogenic strain.

Non-pathogenic *M. bovis* strains that have a disruption in one or more nucleic acid sequences, and immunogenic compositions that include such non-pathogenic *M. bovis* strains, can be administered to cattle to induce a protective response against pathogenic *M. bovis* that lack such disruptions. The term "protective," as used herein, refers to the complete prevention of the disease symptoms, a lessening in the severity or duration of disease symptoms, a delay in onset of the symptoms of a disease, and combinations thereof. Such non-pathogenic *M. bovis* strains can be used as effective vaccines, since they prime the immune system against subsequent infection, yet do not induce a full suite of symptoms of the disease that would otherwise be induced by their pathogenic counterparts.

In some cases, vaccination with a non-pathogenic *M. bovis* strain can result in a protective response in which clinical symptoms are reduced in severity by 50%, 60%, 70%, 80%, 90%, 95%, 96%, 97%, 98%, 99% or 100% (e.g., as determined by standard quantitative measures appropriate for the disease of interest) after challenge with a pathogenic *M. bovis* strain, as compared to the clinical symptoms exhibited by a non-vaccinated animal challenged with the pathogenic *M. bovis* strain. Examples of clinical symptoms that can be reduced in severity include, without limitation, fever, coughing, rapid or labored breathing, inflammation (e.g., of the udders), swelling of the joints, and combinations thereof. In some cases, vaccination with a non-pathogenic *M. bovis* strain can result in a protective response in which clinical symptoms are reduced in severity to such an extent that the animal lives after challenge with a pathogenic *M. bovis* strain, while a non-vaccinated animal challenged with the pathogenic *M. bovis* strain exhibits clinical symptoms of such severity as to result in death. In some cases, vaccination with a non-pathogenic *M. bovis* strain can result in a protective response in which clinical symptoms that are reduced in duration by 50%, 60%, 70%, 80%, 90%, 95%, 96%, 97%, 98%, 99% or 100% after challenge with a pathogenic *M. bovis* strain, as compared to the clinical symptoms exhibited by a non-vaccinated animal challenged with the *M. bovis* pathogenic strain.

Vaccines provided herein (e.g., vaccines containing live, non-pathogenic *M. bovis* bacteria) can exhibit several advantages over vaccines containing inactivated (e.g., killed) *M. bovis* bacteria. For example, killed vaccines typically require weeks to provide protection, while live vaccines such as those provided herein can provide protection within days. In addition, currently available killed *M. bovis* vaccines typically exhibit a poor ability to protect cattle against disease, and if administered repeatedly, can actually enhance the disease upon infection. Furthermore, killed vaccines often require the use of adjuvants that are not suitable in certain situations. For example, lactating dairy cows can react to certain adjuvants commonly used in killed vaccines, which may lead to a decrease in milk production. In contrast, a live vaccine does not require use of an adjuvant, thus avoiding such adverse reactions. Use of a live vaccine circumvents these and other disadvantages.

In some cases, a combination of two or more (e.g., 2, 3, 4, 5, 6, 7, 8, 9, 10, or more) discrete non-pathogenic strain strains of *M. bovis*, or compositions that include two or more discrete strain strains of *M. bovis*, can be administered to cattle to induce an immunogenic response, a protective response, or both. For example, each discrete non-pathogenic strain can include a disruption in one or more nucleic acid sequences as compared to a naturally or non-naturally occurring strain of *M. bovis*. A vaccine containing a combination of two or more discrete non-pathogenic strains of *M. bovis* can exhibit advantageous characteristics over a vaccine containing only a single strain such as, without limitation, improved efficacy, reduced severity or duration of side effects when administered to cattle, increased shelf life, the ability to be used at reduced dosages or with fewer boosters, and combinations thereof. In some cases, discrete non-pathogenic strains of *M. bovis* used in combination can include at least one disruption which is common among two or more of the strains. In some cases, discrete non-pathogenic strains of *M. bovis* used in combination can include at least one disruption which is not common among the strains. In some cases, discrete non-pathogenic strains of *M. bovis* used in combination can include both at least one disruption which is common among two or more of the strains and at least one disruption which is not common among the strains.

In some cases, a vaccine provided herein can include one or more additional components such as a carrier, an immunomodulatory agent, and combinations thereof. Such additional components typically do not generate an immune or protective response themselves, but can enhance the immune or protective response mounted by the host against other immunogenic components of the vaccine (e.g., a live non-pathogenic *M. bovis* strain).

For example, a vaccine can include one or more carriers. As used herein, the term "carrier" includes, without limitation, any of a variety of veterinary-acceptable solvents, dispersion media, coatings, stabilizing agents, diluents, preservatives, antibacterial and antifungal agents, isotonic agents, adsorption delaying agents, and combinations thereof. Diluents can include, without limitation, water, saline, dextrose, ethanol, glycerol, and combinations thereof. Isotonic agents can include, without limitation, sodium chloride, dextrose, mannitol, sorbitol, lactose, and combinations thereof. Stabilizers can include, for example, albumin. In some cases, a vaccine can include one or more immunomodulatory agents such as, e.g., interleukins, interferons, or other cytokines.

A vaccine provided herein (e.g., a vaccine containing a non-pathogenic *M. bovis* strain that has a disruption in one or more nucleic acid sequences as compared to a reference *M. bovis* strain) can be administered in combination with one or more (e.g., 2, 3, 4, 5, 6, 7, 8, or more) other vaccines used to prevent other infectious diseases in cattle. For example, other vaccines that can be administered to cattle in combination with an *M. bovis* vaccine can include, without limitation, bovine herpesvirus type 1 (BHV-1), bovine viral diarrhea virus (BVDV), bovine respiratory syncitial virus (BRSV), parainfluenza virus (PI3), *Pasteurella multocida, Haemophilus somnus, Mycoplasma mycoides, Mycoplasma agalactiae, Mycoplasma californicum, Mycoplasma bovirhinis, Mycoplasma dispar, Mycoplasma canis, Manheimia haemolytica, Moraxella bovis, Moraxella bovoculi, Leptospira* spp., *Clostridia*, and combinations thereof. Individual vaccines of such a vaccine combination can be administered to bovine individuals simultaneously or sequentially.

In some cases, a vaccine provided herein (e.g., a vaccine containing a non-pathogenic *M. bovis* strain that has a disruption in one or more nucleic acid sequences as compared to a reference *M. bovis* strain) can include one or more additional immunogenic agents in the same vaccine. For example, a vaccine containing such a non-pathogenic *M. bovis* strain can include a second non-pathogenic bacterial strain, which second strain is not an *M. bovis* strain. In some cases, a vaccine containing such a non-pathogenic *M. bovis* strain can include a viral immunogen. For example, a viral immunogen can be an inactivated (e.g., heat killed) virus that is not capable of causing disease in cattle. In some cases, a vaccine containing such a non-pathogenic *M. bovis* strain can include an immunogenic polypeptide of a bacterial or viral antigen, or a fragment thereof.

A vaccine provided herein can be administered orally, transdermally, intravenously, subcutaneously, intramuscularly, intraocularly, intraperitoneally, intrarectally, intravaginally, intranasally, intragastrically, intratracheally, intrapulmonarily, or any combination thereof For example, a vaccine that includes a non-pathogenic *M. bovis* strain having a disruption in one or more nucleic acid sequences as compared to a reference strain can be administered intranasally. In some cases, a vaccine can be administered via an animal's food or water supply.

A suitable dose of non-pathogenic *M. bovis* for administration to cattle can be any appropriate dose that elicits an immune response in a bovine animal and optionally protects the animal against disease upon exposure to a pathogenic *M. bovis* strain, but which does not cause significant adverse clinical symptoms upon administration. In some cases, an animal can be immunized by administering at least about $10^3$, $10^4$, $10^5$, $10^6$, $10^7$, $10^8$, $10^9$, *M. bovis* colony forming units ("CFUs") to the animal.

In some cases, cattle are immunized by administering a low vaccinal dose to prevent undesirable effects. For example, in the case where the genome of an *M. bovis* bacterium to be injected includes a transposon that is capable of subsequent transposition (e.g., where such a transposon disrupts a nucleic acid sequence involved in pathogenesis), the practitioner may administer a low vaccinal dose to prevent a secondary transposition or reversion event during in vivo replication. For example, a low vaccinal dose can be about $10^4$ *M. bovis* CFUs or lower.

A suitable vaccinal dose can depend on factors such as, without limitation, the route of administration; the nature of the vaccine; the weight, age, and sex of the bovine animal; the concurrent administration of other vaccines or drugs; the prevalence or threat of infectious diseases; and the judgment of an attending veterinarian. Wide variations in the amount of a suitable dose are to be expected in view of the variety of compositions that can be administered, the variety of cattle to which the composition can be administered, and the differing efficiencies of various routes of administration. For example, oral administration typically requires a higher dose than administration by intramuscular injection to achieve a similar immune or protective response. Variations in dose levels can be adjusted using standard empirical routines for optimization. Encapsulation of the composition in a suitable delivery vehicle (e.g., polymeric microparticles or implantable devices) can increase the efficiency of delivery, particularly for oral administration.

A vaccine provided herein can be administered to cattle prior to infection by a pathogenic *M. bovis* strain. In some cases, a single administration can be sufficient to confer protection from *M. bovis* infection. In some cases, one or more booster immunizations can be administered to enhance or maintain protection. The time interval from the initial immunization to the booster immunization, or between booster immunizations, can vary depending on the age and condition of the animal. For lactating and adult animals, a first vaccination can be given at the end of the lactation cycle, followed by a booster immunization dose twenty-four weeks later. Optional subsequent booster immunizations can be administered. Newborn calves can be vaccinated at birth, and booster immunizations can optionally be administered. For example, booster immunizations can be administered every 3-5 weeks until the calves are 4-6 months old and annually thereafter. In general, animals at risk of infection can be vaccinated as early as possible and can optionally be administered one or more booster immunizations. Booster immunizations can be administered by a different route, at a different vaccinal dosage, or both than the initial immunization.

In some cases, one or more non-pathogenic *M. bovis* bacteria of unknown vaccinal efficacy can be tested for their ability to be used as vaccines. For example, such non-pathogenic *M. bovis* bacteria can be administered to test cattle, which test cattle can be tested for resistance to infection by *M. bovis*. For example, after immunization, test cattle can be challenged with a single dose or multiple doses of a pathogenic *M. bovis* strain. The challenged cattle can be observed for pathologic symptoms characteristic of *M. bovis* infection, such as mastitis, pneumonia, arthritis, otitis, skin abscesses, infertility, abortion, morbidity, mortality, or combinations thereof. In addition, challenged test cattle can be euthanized at various time points, and their tissues (e.g., bronchial lymph nodes, lower tracheal mucosa, upper tracheal mucosa, tonsils, nasal mucosa, mammary glands, or combinations thereof) can be assayed for relative or absolute levels of *M. bovis* using standard methods (e.g., bacterial cultures, ELISA). In some cases, euthanized challenged test cattle can be assayed for internal signs of infection such as, for example, lung lesions. The data obtained with the challenged test cattle can be compared to those obtained with a control group, e.g., cattle that were exposed to a diluent in which the non-pathogenic *M. bovis* bacteria were suspended (e.g., physiological saline), or cattle that were exposed to an adjuvant without the non-pathogenic *M. bovis* bacteria if adjuvant was used for immunization. The control group also can be cattle immunized with a heat, radiation, or chemically killed *M. bovis* preparation (e.g., a formalin treated bacterial preparation) or a vaccine containing such an *M. bovis* preparation. Increased resistance of the test cattle to infection relative to one or more of the control groups can indicate that the non-pathogenic *M. bovis* bacterium is a candidate that can be used to manufacture an effective vaccine.

This document also provides methods and materials for generating live non-pathogenic *M. bovis* bacteria. In some cases, a multi-step approach can be used to generate such live non-pathogenic *M. bovis* bacteria, in which at least two nucleic acid sequences of a parental *M. bovis* bacterium are disrupted. Such a multi-step approach is advantageous since it can result in an *M. bovis* bacterium having at least two nucleic acid sequence disruptions. Increasing the number of nucleic acid sequence disruptions can decrease the chance of reversion (e.g., by recombination with a wild type bacterium) back to the parental strain.

As used herein, the term "parental" refers to a starting bacterium, which starting bacterium is subjected to one or more nucleic acid sequence disruptions. In some cases, a parental bacterium is *M. bovis*. A parental bacterium can be either pathogenic or non-pathogenic. In some cases, a parental bacterium can be naturally occurring or non-naturally occurring. For example, a parental bacterium can be pathogenic *M. bovis* strain M23.

In some cases, a live non-pathogenic *M. bovis* bacterium generated by a multi-step approach can be non-pathogenic as compared to the parental bacterium. For example, an animal exposed to a live non-pathogenic bacterium generated by such a multi-step approach can exhibit clinical symptoms that are reduced in severity by 50%, 60%, 70%, 80%, 90%, 95%, 96%, 97%, 98%, 99% or 100% (e.g., as determined by standard quantitative measures) as compared to the clinical symptoms exhibited by an animal exposed to the parental bacterium. In some cases, an animal infected with a non-pathogenic *M. bovis* bacterium generated by such a multi-step approach can exhibit clinical symptoms that are reduced in severity to such an extent that the animal lives after being infected, while an animal infected with the parental bacterium exhibits clinical symptoms of such severity as to result in death. In some cases, an animal exposed to a live *M. bovis* non-pathogenic bacterium generated by such a multi-step approach can exhibit clinical symptoms that are reduced in duration by 50%, 60%, 70%, 80%, 90%, 95%, 96%, 97%, 98%, 99% or 100% as compared to the clinical symptoms exhibited by an animal exposed to the parental bacterium.

In some cases, a first nucleic acid sequence of a parental bacterium can be disrupted. A first nucleic acid sequence to be disrupted can include a nucleic acid sequence encoding or controlling expression of a polypeptide such as, without limitation, one or more of the nucleic acid sequences listed in Table 1. In some cases, a nucleic acid sequence to be disrupted encodes or controls expression of an *M. bovis* polypeptide such as, without limitation, a p59 polypeptide, a p48 polypeptide, an 1poA polypeptide, an oppA polypeptide, an oppB polypeptide, an oppC polypeptide, an oppD polypeptide, a p59 polypeptide, a p59 polypeptide, or a polypeptide homologous to any of the *M. agalactiae* MAG 0150 polypeptide, the *M. agalactiae* MAG 0160 polypeptide, or *M. agalactiae* MAG 28000 polypeptide. Any first parental nucleic acid sequence can be disrupted, so long as the disruption results in an *M. bovis* bacterium that is non-pathogenic as compared to the parental bacterium.

A parental nucleic acid sequence can be disrupted by any of a variety of methods including, but not limited to, nucleic acid insertions (e.g., transposition events and single amino acid insertions), deletions, substitutions, and combinations thereof. For example, a first nucleic acid sequence of a parental bacterium can be disrupted by insertion of a "nucleic acid insert". The term "nucleic acid insert" as used herein with reference to a disruption refers to a nucleic acid sequence that is inserted into a first parental nucleic acid sequence, which upon insertion, disrupts the function of the first parental nucleic acid sequence. A nucleic acid insert can be of any length. For example, a nucleic acid insert can be up to 10, up to 20, up to 30, up to 40, up to 50, up to 60, up to 70, up to 80, up to 90, up to 100, up to 150, up to 200, up to 250, up to 300, up to 350, up to 400, up to 450, up to 500, up to 600, up to 700, up to 800, up to 900, up to 1000, or more nucleotides in length. A nucleic acid insert can include any sequence. Exemplary nucleic acid inserts can include, without limitation, transposons (e.g., Tn4001, Tn4001mod, pRIT), nucleic acid sequences encoding marker polypeptides (e.g., polypeptides that provide antibiotic resistance or nucleic acid sequences that encode a marker such as lacZ), non-coding nucleic acid sequences, and combinations thereof. In some cases, nucleic acid inserts can include sequences that are present in a naturally occurring or non-naturally occurring organism (e.g., a transgenic organism). In some cases, nucleic acid inserts can include sequences from vectors (e.g., bacterial, mammalian, or insect vectors) such as plasmids, cosmids, phagemids, BACs, and combinations thereof. In some cases, nucleic acid inserts can include sequences that do not occur in any organism or vector. For example, nucleic acid inserts can be chemically synthesized.

In some cases, a nucleic acid insert can be a provided in a vector that includes sequences homologous to a first parental nucleic acid sequence to be disrupted, such that site-specific homologous recombination can occur. Such a vector can include one or more selection markers (e.g., nucleic acid sequences that encode antibiotic resistance polypeptides), and bacteria containing the vector can be grown under selective pressure to ensure that the vector is retained in the bacteria, increasing the likelihood of site-specific homologous recombination into the first parental nucleic acid sequence. In some cases, such a vector can include an origin of replication that functions in *M. bovis*. Such an origin of replication can include, for example, a sequence that includes the oriC region of the *M. bovis* genome, or a homologous sequence.

In some cases, after site-specific homologous recombination, bacteria can be relieved of selective pressure (e.g., grown in the absence of antibiotics) such that the vector is lost from the bacteria. A successful site-specific homologous recombination event can result in the selection marker being inserted into the first parental nucleic acid sequence. Selection pressure can subsequently be re-applied to identify bacteria that have undergone a successful site-specific homologous recombination event. Any of a variety of appropriate techniques can be used to verify the presence of a nucleic acid insert in the first parental nucleic acid sequence such as PCR, Southern blotting, nucleic acid chip analysis, and combinations thereof In some cases, site-specific homologous recombination can be verified by appropriate screens or selection strategies in cases where the first parental nucleic acid sequence has a function that can be identified by screening or selection, which function is disrupted by the site-specific homologous recombination event.

In some cases, a nucleic acid insert can include an excision sequence. The term "excision sequence" as used herein with reference to a nucleic acid insert refers to a nucleic acid sequence that facilitates excision of at least part of the nucleic acid insert upon recognition by a suitable agent under suitable conditions. For example, an excision sequence can include a site-directed excision sequence such as Flipase Recognition Target (FRT) sites or Lox sites. FLP sites are short 22 base pair elements recognized by the Flipase (FLP) enzyme, which directs excision of the FLP sites from DNA, as well as any intervening nucleic acid sequences positioned between the FLP sites. Similarly, Lox sites are recognized by the Cre enzyme, which directs their excision. Other site-directed excision systems can be used.

In some cases, a nucleic acid insert containing an excision sequence can be excised from the first parental nucleic acid sequence by subjecting the bacterium to an agent that directs excision of the excision sequence. For example, FRT sites can be excised upon recognition by a FLP recombinase enzyme. A nucleic acid insert that includes FRT sites can be excised from the target nucleic acid sequence by subjecting the bacterium to a FLP recombinase enzyme. Such a FLP recombinase enzyme can be provided in any of a variety of ways. For example, a bacterium that contains a nucleic acid insert that contains FRT sites can be transformed with a vector that includes a nucleic acid sequence encoding a FLP recombinase enzyme, which FLP recombinase enzyme can be expressed in the bacterium. The p81 promoter (SEQ ID NO: 3, FIG. 4) is an example of a promoter that can be used to direct expression of polypeptides in *M. bovis* strains such as *M. bovis* strain M23. In some cases, an inducible promoter can be used to direct expression of a polypeptide excision agent. In some cases, a heat-inducible promoter can be used. Examples of heat-inducible promoters include, without limitation, clpB and lonA from *M. bovis*. Upon excision of the FRT-containing nucleic acid insert, a residual disrupting insertion of short length and known sequence can be present at the site of the first parental nucleic acid sequence, thus disrupting the function of the first parental nucleic acid sequence.

In some cases, a second nucleic acid sequence of a parental bacterium can be disrupted. For example, a second nucleic acid sequence can be disrupted by any of the techniques described herein. A second nucleic acid sequence to be disrupted can include a nucleic acid sequence encoding or controlling expression of a polypeptide such as, without limitation, one or more of the nucleic acid sequences listed in Table 2. In some cases, a nucleic acid sequence to be disrupted encodes or controls expression of an *M. bovis* polypeptide such as, without limitation, a potC polypeptide, a hemK polypeptide, a oppF polypeptide, or a deoA polypeptide.

In some cases, a second nucleic acid sequence of a parental bacterium can be disrupted by inserting a nucleic acid insert without subsequent removal of that nucleic acid insert (e.g., via an excision sequence) such that second nucleic acid sequence is disrupted by the nucleic acid insert. Such a disruption strategy can be especially advantageous when the disruption cannot be reversed, for example by spontaneous excision of the nucleic acid insert. A second nucleic acid sequence can be disrupted by inserting a nucleic acid insert containing a marker that can be identified by appropriate selection or screening techniques. One non-limiting example of such a marker is the lacZ polypeptide. A second nucleic acid sequence that has been disrupted by insertion of a nucleic acid sequence encoding a lacZ polypeptide can be screened by traditional strategies such as IPTG/X-gal screening. Another non-limiting example of such a marker is an antibiotic resistance polypeptide. Bacteria containing a nucleic acid sequence encoding such an antibiotic resistance polypeptide can be screened using selective media containing the antibiotic.

In some cases, a second nucleic acid sequence of a parental bacterium can be disrupted by transforming the bacterium with a vector that contains a selectable or screenable (e.g., lacZ) marker, which marker is flanked by sequences homologous to the second nucleic acid sequence to be disrupted. Site-specific recombination between the vector and the second parental nucleic acid sequence can result in removal of all or part of the second parental nucleic acid sequence and insertion of the screenable or selectable marker, which can be identified as described herein. In some cases, homologous sequences of such a vector can flank the second parental nucleic acid sequence such that site-specific homologous recombination with the second parental nucleic acid sequence removes the second parental nucleic acid sequence entirely.

In some cases, one or more additional (e.g., third, fourth, fifth) nucleic acid sequences of a parental bacterium can be disrupted by any of the variety of methods provided herein.

Live non-pathogenic *M. bovis* bacteria generated by disrupting at least two parental nucleic acid sequences can be used in the preparation of any of a variety of vaccines. A vaccine containing a live non-pathogenic *M. bovis* bacterium that includes a disruption in two or more nucleic acid sequences (e.g., a nucleic acid sequence listed in Table 1 and a nucleic acid sequence listed in Table 2) can be advantageous since the chance of reversion to the parental strain after vaccination is extremely small. For example, should such a live non-pathogenic *M. bovis* bacterium be exposed to and conjugate with a parental or otherwise pathogenic strain that includes the parental nucleic acid sequence, such that one nucleic acid sequence containing a disruption reverts to the parental nucleic acid sequence (e.g., by recombination of genetic material after conjugation), the other nucleic acid sequence disruption(s) can be maintained, and the *M. bovis* bacterium can remain non-pathogenic. Use of vaccines containing live non-pathogenic *M. bovis* bacteria having a disruption in at least two parental nucleic acid sequences can provide a measure of protection should conjugation and genetic recombination occur in these organisms.

In some cases, a live non-pathogenic *M. bovis* bacterium generated by any of the methods provided herein can lack an exogenous antibiotic marker. For example, in cases where one or more parental nucleic acid sequences are disrupted by inserting an antibiotic marker into a parental nucleic acid sequence of interest, such an antibiotic marker can be removed (e.g., via excision). Such *M. bovis* bacteria lacking exogenous antibiotic markers can be advantageous for a variety of reasons. For example, lacking an exogenous antibiotic marker, such bacteria cannot spread exogenous antibiotic resistance to cattle, other pathogens, or other organisms in the wild.

EXAMPLES

Example 1

Tetracycline Expression in *M. Bovis*

The pathogenic *M. bovis* strain M23 was transformed with plasmids pISM 1002 and Tn4001miniTet. pISM 1002 harbors a 4.8 kb nucleic acid sequence encoding tetracycline. pISM 1002 has an origin of replication for *E. coli* but no origin of replication for mycoplasma. Tn4001miniTet carries a Tn4001 transposon element (including inverted repeated sequences) and a nucleic acid sequence encoding tetracycline, but lacks an origin of replication for *M. bovis*. No transformants were obtained with either pISM 1002 or Tn4001miniTet (at a detection limit of <5×10$^8$) in *M. bovis*. One possible cause of the observed lack of transformants may be the short half-life of the transformed plasmids in *M. bovis* and the large size of the tetracycline-encoding nucleic acid.

In order to construct self-replicative plasmids that will have longer half-life in the transformed mycoplasma cell, a genome fragment of *M. bovis* was obtained and tested for the presence of an origin of replication. The sequence obtained included the traD, dnaA, and dnaN genes. Analysis of the genomic fragment revealed clusters of 3 DnaA binding boxes flanking the sequence of the dnaA gene that could potentially function as an oriC origin of replication. These clusters were in a region of 170 basepair upstream of dnaA, and a region of 133 basepair downstream of dnaA. Three constructs were cloned into pISM 1002 at the unique EcoRI site of the vector. A fragment of about 1.7 kb contained the upstream region, dnaA, and the downstream region (SEQ ID NO: 1. FIG. 1). A 170 basepair construct contained only the upstream sequence, and a 133 basepair construct contained only the downstream sequence (SEQ ID NO: 2, FIG. 2). The constructs were verified by sequencing and designated pMbOR-1, pMbOR-2, and pMbOR-3, respectively (FIG. 3).

The pMBOR-1 plasmid was constructed using two primers (Forward Primer 1: GAATTCgcttgatacaatcat (SEQ ID NO: 4) and Reverse Primer 1: GAATTCtttacaataattttcat (SEQ ID NO: 5)) that were engineered to contain EcoRI restriction site sequences (nucleotides in capital case), such that both ends of the PCR amplicon generated with these primers contained EcoRI sites. *M. bovis* M23 DNA template DNA was amplified by PCR using Forward Primer 1 and Reverse Primer 1, and the PCR amplicon was digested with EcoRI and ligated into pISM 1002.

The pMBOR-3 plasmid was constructed using two primers (Forward Primer 2: GAATTCttaagaaaagttaa (SEQ ID NO: 6) and Reverse Primer 2: GAATTCtttacaataatttca (SEQ ID NO: 7)) that were engineered to contain EcoRI restriction site sequences (nucleotides in capital case), such that both ends of the PCR amplicon generated with these primers contained EcoRI sites. *M. bovis* M23 DNA template DNA was amplified by PCR using Forward Primer 2 and Reverse Primer 2, and the PCR amplicon was digested with EcoRI and ligated into pISM 1002.

Mid-log grown *M. bovis* were transformed with 1 μg of plasmid DNA. The transformed cells were spread onto Friis plate supplemented with tetracycline (2 μg/mL) and incubated at 37° C. for 3 days. Colonies were counted under inverted microscopy. Transformation frequencies obtained on the Friis agar plates for pMbOR-1, pMbOR-2, and pMbOR-3 were 1.53×10$^{-5}$, 0, and 1.27×10$^{-5}$, respectively. The transformation frequency was determined by dividing tetracycline resistant colonies by total numbers of colonies plated on agar plate. Furthermore, transformation frequency of this plasmid was considerably higher than transformation frequencies reported for several other mycoplasma strains.

When *M. bovis* was transformed with pMBOR-3, the resulting transformants rapidly lost the free plasmid replicons if tetracycline selective pressure was removed. Moreover, the pMBOR-3 transformants also did not survive high-level tetracycline selective pressure (40 μg/mL). In contrast, transformation with pMbOR-1 resulted in transformants that had tetM integrated into the *M. bovis* chromosome. Additionally, the pMbOR-1 transformants survived both absence of tetracycline selective pressure and high level tetracycline selective pressure.

These results demonstrate that pMbOR-3 containing the 133 basepair construct downstream of the dnaA gene was sufficient to permit replication of the plasmid. These results also demonstrate that the tetM gene can be expressed in *M. bovis* under its own promoter.

Example 2

Selection of an Avirulent *M. Bovis* Strain

Strain M31 of *M. bovis* was passed 100 times (about 900 doublings) in vitro to reduce pathogenicity. The resulting strain (strain M31hi) was then tested for phenotype. The initial strain (M31lo) was minimally cytotoxic, non-invasive (in vivo test), and capable of inducing immunosuppression. Cytotoxicity, defined as percent of mycoplasma colonies that can kill apposed mammalian cells in vitro was still evident in a small proportion of the M31hi cell population. A lineage from a non-cytotoxic colony filter-cloned and final stock of M31hi that was 100% non-cytotoxic was derived. The strain gave 100% of colonies expressing VspA and VspL, as tested by immunoreaction of colony lifts with specific antibodies, indicating that the strain had not suffered significant phenotypic changes in surface protein expression.

This M31hi lineage was then tested for surface protein phenotype and ability to adhere to bovine lung epithelial cells in vitro. Pathogenic strain M2310 exhibited an adherence index of 22.4×10$^3$ (ratio of radioactive *M. bovis* binding to a monolayer of bovine lung epithelial cells over total radioactive *M. bovis* added to well). In contrast, strain M31hi exhibited an adherence index of 31.5×10$^3$, statistically higher ($p<0.05$) than the pathogenic M2310 strain, and similar to several high adherence field strains. The M31hi strain qualified as a good candidate for use in an intranasal vaccination mode, since it can readily adhere to respiratory epithelium and undergo replication.

Transformations with Tn4001mod plasmids with or without the oriC region of *M. bovis* M31 did not lead to recovery of mutants. Attempts to force integration of the transforming plasmid under temperature extremes also did not lead to recovery of mutants. It is possible that this strain has a unique restriction/modification system that destroys foreign DNA, and in particular, the tetM gene sequences needed for selection.

Example 3

Construction of a Removable Tc Marker

Plasmid pLOI 2227 was obtained from Dr. Ingram (University of Florida). A 280 basepair FRT-flanked cassette from pLOI 2227 was cloned into a pKS plasmid. The resulting construct contained two FRT sites flanking a multiple cloning site (MCS), as well as a second MCS. The tetM gene from plasmid pISM 1002 was then inserted into the MCS flanked by FRT sites.

A single cross-over insertion strategy was developed to enhance the chances of obtaining non-immunosuppressive mutants of *M. bovis*, since a single cross-over recombination event is expected to occur ~100 times more frequently than a double cross-over recombination event. A single cross-over insertion strategy does not permit removal of the tetracycline marker from the *M. bovis* mutant. That is, an avirulent vaccine strain generated by a single cross-over event can carry resistance to tetracycline.

Example 4

Generation of a Transposon Based Library of *M. bovis*

The following was attempted to construct random mutants of *M. bovis* with three different transposon-based plasmids.

The transformation frequencies achieved with these plasmids were summarized (Table 3). With plasmid Tn4001 (containing a miniTetM), no mutants were obtained. Plasmid pISM 2062 was not applicable to construct mutants because *M. bovis* strain M23 is naturally resistant to gentamicin, a selection marker for pISM 2062. Transformation with plasmid pRIT (containing TetM, Tn916, and sequences of *M. pulmonis*) resulted in 18 mutants, with a transformation frequency of about $6.8 \times 10^6$.

TABLE 3

Transformation frequency of transposon-based plasmids.

| Plasmid | Total CFU[a] | TcR CFU[b] | Transformation frequency[c] |
|---|---|---|---|
| No DNA (spontaneous mutants) | $3.66 \times 10^9$ | 0 | 0 |
| pISM 1002 | $3.10 \times 10^9$ | 0 | 0 |
| Tn4001 miniTet | $2.50 \times 10^9$ | 0 | 0 |
| pISM 2062 (gentamicin) | Not usable[d] | | |
| pRIT | $9.0 \times 10^8$ | 132 | $3.1 \times 10^{-6}$ |

[a]Total colony forming units (CFU) was the total number of colonies obtained on non-selective agar plates after electroporation.
[b]Tetracycline resistant CFU was the total number of colonies on selective agar plate supplement with 2 µg/mL tetracycline after electroporation, followed by a two hour incubation at 37° C.
[c]Calculated as TcR CFU/total CFU
[d]*Mycoplasma bovis* M23 strain is naturally resistant to gentamicin which is a selection maker for pISM 2062.

These results demonstrate the successful transformation of *M. bovis* with pRIT, a large tetM-carrying plasmid containing Tn916, and demonstrate that it is possible to generate transposon-mediated mutations in this organism.

Example 5

Identification of Transposon Insertion Sites in Random Mutants of *M. Bovis*

A plasmid capable of generating random mutants of *M. bovis* was constructed. The plasmid contained all components required for Tn4001 functionality, as well as tetracycline resistance. Using this plasmid, 3,155 mutants were generated. Genomic DNA was extracted from 306 mutants for further analysis.

For sequencing the mutants, a universal primer specific to the tetM gene of the plasmid was constructed. To validate the primer functionality, the primer was used to sequence six genomic DNA samples from mutants. The primer worked well in all six samples. To establish a protocol for searching for transposon inserted sites in individual mutants, the DNA-MAN and Blast search programs (NCBI) were used to analyze the sequence of the six samples. The results were summarized (Table 4).

TABLE 4

Identification of insertion sites of Tn4001 in six mutants.

| # of Mutant | Insertion direction | Putative location | DNAMAN/NCBI |
|---|---|---|---|
| Tn 1 | − | Intergenic | |
| Tn 2 | − | Gene (33 kD) | Putative transmembrane protein *M capricolum* (4e−16) *M. mycoides* (5e−15) |
| Tn 3 | + | Intergenic | |
| Tn 4 | + | Intergenic | |

TABLE 4-continued

Identification of insertion sites of Tn4001 in six mutants.

| # of Mutant | Insertion direction | Putative location | DNAMAN/NCBI |
|---|---|---|---|
| Tn 5 | + | Intergenic | |
| Tn 6 | + | Gene (12 kD) | Putative endoglucanase *M. synoviae* 53 (3e−46), 282/388 Amino peptidase *M. pulmonis* UAB (2e−22), 268/398 Amino peptidase *M. hyopneumoniae* 7448 (1e−6), 164/240 Putative amino peptidase *M. hyopneumoniae* 232 (5e−5), 160/240 Endo-1,4-beta-glucanase *M. hyopneumoniae* J (5e−5), 160/240 *M. hyopneumoniae* 232 (5e−5), 160/240 |

Example 6

Development of a Modified-Live Vaccine Against *M. bovis*

64 insertion mutants of *M. bovis* generated as described in Example 5 were tested in a cattle model of pneumonia. Each mutant had a single and known gene insertion with transposon Tn4001mod in a 12 kb construct containing resistance markers for ampicillin, gentamycin, and tetracycline. The background for these mutants was pathogenic strain M23 of *M. bovis*. Using five pairs of mycoplasma-free calves, each pair inoculated was inoculated with pools of 10 to 15 mutants by the intratracheal route at $10^8$ CFU per mutant, a dose that was sufficient for this model. Seven days later, the cattle were euthanized, and mutants were sought on the tracheal mucosa (at the inoculation site), and in the bronchial lymph node (the lymph node draining most of the lung, to which site phagocytic cells would transport any mycoplasma).

Three classes of mutants were identified: (i) a wild type class that could be recovered from the lower tracheal mucosa and the bronchial lymph node, (ii) a phagocyte-sensitive class that could not be recovered from the bronchial lymph node but was recovered from the tracheal mucosa, and (iii) a weak colonizing class that could not be recovered from tracheal mucosa or bronchial lymph node. All mutants were recovered from tonsil, indicating that replication of all mutants occurred to some extent in the calves.

Pairs of mycoplasma-free seven-month-old Holstein steer calves were then infected by intranasal exposure with three inocula: (1) a strain comprising a mutation in potC, a weak-colonizing mutant, which strain was still able to suppress lymphocytes; (2) a strain comprising a mutation in the p59 gene, which codes for a generic ABC transporter polypeptide, which mutant is defective only in lymphocyte suppression, or (3) saline. Since the *M. bovis* mutants were generated by random transposition events and still contained the Tn4001mod transposon, a very low dose of $10^4$ CFU was used to avoid the possibility of secondary transposition or reversion during in vivo replication. Fourteen days after vaccination, all calves were challenged by intratracheal and intranasal exposure to the pathogenic M23 strain. Replication of the M23 strain was allowed to proceed for fourteen days, after which the animals were necropsied. The amount of *M. bovis* at the challenge sites and other sites (tonsil, tracheal mucosa distant from the challenge site, bronchial lymph node) was then quantitated. The extent of lung lesions detected in each steer was also determined.

Neither the potC nor the p59 mutant was recovered from nasal swabs, blood, or tissues of the calves. One possibility for the observed lack of recovery is the very low dose of $10^4$ CFU that was administered. The p59 mutant defective in lymphocyte suppression provided a more robust protective effect against the challenge, when compared to the calves given the potC weak-colonizing mutant or saline, resulting in a significantly decreased (p<0.05) colonization of the challenge in the lower trachea and bronchial lymph node (Table 5). A slight, but not statistically significant, reduction in lung lesions was also observed in the calves given the p59 lymphocyte suppression-defective strain (Table 6). These calves were also the only ones that seroconverted after vaccination (Table 7). All calves seroconverted after challenge. However, those calves vaccinated with the p59 lymphocyte suppression-defective strain reached higher O.D. values, indicating that the vaccination successfully primed the immune system.

TABLE 5

Quantitative recovery (in log10 CFU/mL) of virulent challenge strain from steers vaccinated with mutants.

| Tissue sampled | Type of Vaccination | | |
|---|---|---|---|
| | Control group | Weak-colonizing mutant | Lymphocyte-suppressive mutant |
| Bronchial lymph node | 1 + 1 | 1.5 ± 0.5 | 0 |
| Lower tracheal mucosa | 3 ± 1.5 | 3 ± 0.5 | 0 |
| Upper tracheal mucosa | 2 ± 0 | 1.5 ± 0.5 | 1 ± 1 |
| Tonsil | 2.5 ± 1.5 | 1.5 ± 0.5 | 1 ± 1 |
| Nasal mucosa | Neg | Neg | Neg |

Values are mean + SEM. Comparisons were made horizontally within each tissue type using T-tests. Values in shaded boxes are significantly different (p < 0.05) from the others.

TABLE 6

Lung lesion scores 14 days after challenge with virulent M23 strain.

| | Type of Vaccination | | |
|---|---|---|---|
| | Control group | Weak-colonizing mutant | Lymphocyte-suppressive mutant |
| % Lung affected | 0.07 ± 0.03 | 0.035 ± 0.035 | 0 |

Values are mean + SEM. Comparisons were made among treatments using T-tests.

TABLE 7

Serological responses (ELISA) to M23 strain after vaccination and challenge.

| | Type of Vaccination | | |
|---|---|---|---|
| | Control group | Weak-colonizing mutant | Lymphocyte-suppressive mutant |
| Pre-vaccinal | 0.082 ± 0.008 | 0.082 ± 0.006 | 0.075 ± 0.001 |
| Post-vaccinal | 0.079 ± 0.007 | 0.076 ± 0 | 0.106 ± 0.013 |
| Post-challenge | 0.114 ± 0 | 0.107 ± 0.09 | 0.165 ± 0.033 |

Values are mean + SEM. Comparisons were made vertically within groups. An increase of 0.030 in O.D. indicates seroconversion.
All ELISA tests were run simultaneously.

Example 7

Vectors for Generating *M. bovis* Mutations

Several plasmids were constructed with a truncated but active oriC of *M. bovis* and were able to replicate independently of the genome in transformed *M. bovis* strain M23 cells under antibiotic pressure. Removal of the antibiotic pressure resulted in loss of the independently replicating plasmid. In addition, plasmids were constructed that carried the marker for chloramphenicol resistance, which was expressed in *M. bovis* strain M23 under the control of the promoter of the p81 gene of *M. bovis*, but not under its own promoter. Plasmids expressing lacZ in *M. bovis* M23 under the control of the p81 promoter were also constructed.

Example 8

A Two Step Strategy for Generating *M. bovis* Mutations

The pathogenic M23 strain is transformed with two separate nucleic acid sequence insertions to assure stability and non-pathogenicity of the resulting mutant strain. To insert a gene-inactivating sequence in a first nucleic acid sequence, a looping-out strategy with a plasmid containing the tetM gene and oriC of strain M23 flanked by FRT cassettes is used, which FRT cassettes are flanked by *M. bovis* genome sequences that flank the gene to be interrupted. The vector also contains a functional cat gene driven by the p81 promoter of *M. bovis* located outside the FRT cassettes. Tetracycline-resistant mutants are selected and are passed five times under tetracycline pressure to promote homologous recombination events at the target nucleic acid sequence. Mutants are then passed ten times without tetracycline, such that the non-integrated oriC plasmid is lost from the strain.

Tetracycline-resistant and chloramphenicol-sensitive mutants are then selected, which mutants have a first nucleic acid sequence disrupted by the tetM gene insertion. These mutants are transformed with a small non-integrating plasmid containing oriC of strain M23, a cat gene, and a FLP gene under control of a promoter known to drive expression of polypeptide-encoding nucleic acid sequences in *M. bovis* M23. Mutants selected under chloramphenicol pressure are obtained and tested for loss of tetracycline resistance, since transient expression of the FLP recombinase drives removal of the inserted tetM, resulting in a nucleic acid sequence disruption of short length and known sequence. The resulting mutant(s) are then passed ten times without chloramphenicol to lose the plasmid carrying FLP from the strain, resulting in mutant(s) that are tetracycline and chloramphenicol sensitive.

To disrupt a second nucleic acid sequence, a lacZ expression and positive selection strategy is employed. A transforming pUC 19-derived plasmid is which lacks a nucleic acid sequence encoding ampicillin is used. The transforming pUC 19-derived plasmid contains (i) the oriC of M23, and (ii) a cassette having a nucleic acid sequence containing a lacZ-encoding nucleic acid sequence fused in frame with the 5' end of the p81-encoding nucleic acid sequence and its promoter, which cassette is flanked by sequences that flank the nucleic acid sequence to be disrupted. Blue colonies are selected in X-gal media conditions, picked and filter-cloned onto fresh X-gal plates to obtain discrete blue colonies that are tetracycline sensitive. The double mutants will have the second nucleic acid sequence disrupted by the pUC 19-derived plasmid containing a lacZ-encoding nucleic acid sequence. Such a double mutant devoid of active transposons can be acceptable under USDA review procedures since reversion to virulence of one of the genes (e.g., by conjugation with a virulent strain) will still maintain the other gene as non-virulent.

A nucleic acid sequence encoding a polypeptide that affects lymphocyte suppression is used as first target (e.g., p59), and a nucleic acid sequence encoding a polypeptide that affects colonization (e.g., potC or Hemk) is used as second target. Since both lymphocyte suppression abrogation and weak colonization can result in tonsil recovery of the strain, a mutant strain having disruptions in nucleic acid sequences encoding polypeptides that affect lymphocyte suppression and colonization will be able to prime the immune response while having a limited infectious profile. The dose of such a mutant strain delivered to nasal mucosa is selected to provide an adequate immune response.

OTHER EMBODIMENTS

It is to be understood that while the invention has been described in conjunction with the detailed description thereof, the foregoing description is intended to illustrate and not limit the scope of the invention. Other aspects, advantages, and modifications are within the scope of the following claims.

What is claimed is:

1. An immunogenic composition comprising a pharmaceutically acceptable carrier and a live *Mycoplasma bovis* bacterium comprising a disruption present in at least one nucleic acid sequence, wherein said live *Mycoplasma bovis* bacterium is non-pathogenic as compared to a reference *Mycoplasma bovis* bacterium containing said at least one nucleic acid sequence and lacking said disruption.

2. The immunogenic composition of claim 1, wherein said disruption comprises an insertion.

3. The immunogenic composition of claim 2, wherein said insertion comprises an insertion having a length between 18 and 5500 nucleotides.

4. The immunogenic composition of claim 1, wherein said disruption comprises a deletion.

5. The immunogenic composition of claim 4, wherein said deletion comprises a deletion having a length between 2000 and 4000 nucleotides.

6. The immunogenic composition of claim 1, wherein said at least one nucleic acid sequence encodes a potC polypeptide in said reference *Mycoplasma bovis* bacterium.

7. The immunogenic composition of claim 1, wherein said at least one nucleic acid sequence encodes a polypeptide that controls expression of a potC polypeptide in said reference *Mycoplasma bovis* bacterium.

8. The immunogenic composition of claim 1, wherein said reference *Mycoplasma bovis* bacterium is strain M23.

9. A method of inducing a protective response against *Mycoplasma bovis* in a bovine animal, said method comprising administering an immunogenic composition to said bovine animal, wherein said immunogenic composition comprises a pharmaceutically acceptable carrier and a live *Mycoplasma bovis* bacterium comprising a disruption present in at least one nucleic acid sequence, wherein said live *Mycoplasma bovis* bacterium is non-pathogenic as compared to a reference *Mycoplasma bovis* bacterium containing said at least one nucleic acid sequence and lacking said disruption.

10. The immunogenic composition of claim 1, wherein said live *Mycoplasma bovis* bacterium comprises a first disruption present in a first nucleic acid sequence and a second disruption present in a second nucleic acid sequence;
wherein said live *Mycoplasma bovis* bacterium is non-pathogenic as compared to a reference *Mycoplasma bovis* bacterium containing said first and second nucleic acid sequences and lacking said first and second disruptions.

11. The immunogenic composition of claim 10, wherein said first nucleic acid sequence encodes a p59 polypeptide in said reference *Mycoplasma bovis* bacterium.

12. The immunogenic composition of claim 10, wherein said first nucleic acid sequence encodes a polypeptide that controls expression of a p59 polypeptide in said reference *Mycoplasma bovis* bacterium.

13. The immunogenic composition of claim 10, wherein said second nucleic acid sequence encodes a potC polypeptide in said reference *Mycoplasma bovis* bacterium.

14. The immunogenic composition of claim 10, wherein said second nucleic acid sequence encodes a polypeptide that controls expression of a potC polypeptide in said reference *Mycoplasma bovis* bacterium.

15. The immunogenic composition of claim 10, wherein said second nucleic acid sequence encodes a hemK polypeptide in said reference *Mycoplasma bovis* bacterium.

16. The immunogenic composition of claim 10, wherein said second nucleic acid sequence encodes a polypeptide that controls expression of a hemK polypeptide in said reference *Mycoplasma bovis* bacterium.

17. The immunogenic composition of claim 10, wherein said reference *Mycoplasma bovis* bacterium is strain M23.

18. The immunogenic composition of claim 10, wherein said live *Mycoplasma bovis* bacterium lacks an exogenous nucleic acid sequence encoding a polypeptide having antibiotic resistance activity.

19. The composition of claim 10, wherein said live *Mycoplasma bovis* bacterium lacks a Tn4001mod transposon.

20. A method for reducing *Mycoplasma bovis* colonization in a bovine animal exposed to pathogenic *Mycoplasma bovis* bacteria, said method comprising administering an immunogenic composition to said bovine animal, wherein said immunogenic composition comprises a pharmaceutically acceptable carrier and a live *Mycoplasma bovis* bacterium comprising a disruption present in at least one nucleic acid sequence, wherein said live *Mycoplasma bovis* bacterium is non-pathogenic as compared to a reference *Mycoplasma bovis* bacterium containing said at least one nucleic acid sequence and lacking said disruption.

21. The method of claim 20, wherein said pathogenic *Mycoplasma bovis* bacteria colonize a tissue selected from the group consisting of bronchial lymph nodes, lower tracheal mucosa, upper tracheal mucosa, tonsils, nasal mucosa, mammary glands, and combinations thereof.

22. A method of generating a live *Mycoplasma bovis* bacterium, wherein said method comprises disrupting a first nucleic acid sequence and a second nucleic acid sequence in a parental *Mycoplasma bovis* bacterium to generate said live *Mycoplasma bovis* bacterium
wherein said live *Mycoplasma bovis* bacterium is non-pathogenic as compared to said parental *Mycoplasma bovis* bacterium that lacks said first and second nucleic acid sequence disruptions.

23. The method of claim 22, wherein disrupting said first nucleic acid sequence comprises inserting a first nucleic acid insert into said first nucleic acid sequence.

24. The method of claim 23, wherein said first nucleic acid insert comprises an excision sequence.

25. The method of claim 24, wherein said method comprises providing an agent that recognizes said excision sequence, which agent causes said excision sequence to be excised from the first nucleic acid sequence.

26. The method of claim 25, wherein said first nucleic acid insert comprises a transposon, said excision sequence comprises Flipase Recognition Target (FRT) sequences, and said agent comprises a Flipase (FLP) recombinase.

27. The method of claim 22, wherein disrupting said second nucleic acid sequence comprises inserting a second nucleic acid insert into said second nucleic acid sequence.

28. The method of claim 22, wherein said live *Mycoplasma bovis* bacterium lacks a Tn4001mod transposon.

29. The method of claim 22, wherein said live *Mycoplasma bovis* bacterium lacks an exogenous nucleic acid sequence encoding a polypeptide having antibiotic resistance activity.

30. The method of claim 22, wherein said first nucleic acid sequence encodes a p59 polypeptide or controls expression of a p59 polypeptide in said parental *Mycoplasma bovis* bacterium, said second nucleic acid sequence encodes a potC polypeptide or controls expression of a potC polypeptide in said parental *Mycoplasma bovis* bacterium, or both.

31. An isolated nucleic acid molecule comprising a sequence selected from the group consisting of: SEQ ID NO: 1, a sequence that is at least 90% identical to SEQ ID NO: 1, SEQ ID NO: 2, and a sequence that is at least 90% identical to SEQ ID NO: 2.

32. A vector comprising an isolated nucleic acid molecule comprising a sequence selected from the group consisting of: SEQ ID NO: 1, a sequence that is at least 90% identical to SEQ ID NO: 1, SEQ ID NO: 2, and a sequence that is at least 90% identical to SEQ ID NO: 2.

* * * * *

SEQUENCE LISTING

<160> NUMBER OF SEQ ID NOS: 3

<210> SEQ ID NO 1
<211> LENGTH: 1719
<212> TYPE: DNA
<213> ORGANISM: Mycoplasma bovis

<400> SEQUENCE: 1

```
ttttattaat tatagagcaa taataacctt atgaattaaa ttaagctcat taatagtcaa      60
actacatatt aacaatgaac tgtggataac ttgttagaat actgtggata acttgttata     120
taaacacttt ataaactaac aatattaatt attatttatt atttatatat gaatatcaat     180
agcactaatg ataaggaaat tgctttaaag tcttacactg aaacctttt agatattctg      240 agacaagaat taggcgatca gatgctttat aaaaactttt ttgcaaattt tgaaatcaaa     300
gatatttcaa aaataggcca cataacaatt ggaacaacaa acataacacc taattctcaa     360
tatgtgatca aagcttatga aagtagcata caaaaatctc ttgatgaaac atttgaacgc     420
aaatgtacat ttagctttgt tttacttgat tcagctataa aaagaagat aaaacgcgaa      480 agaaaagaag aggcaattga aaatattgaa ttgtcaaatc gtgaagtcga caaaactaaa     540
acatttgata attatgtaga aggcaacttt aataaagaag ccatcagaat agcaaaatta     600
attgtcgatg gtgaagaaga ctataatcca atatttattt atgggaaatc cggaataggt     660
aaaacacact tactcaacgc catatgtaat gagtttctta aaaaagatgt tacagttaaa     720
tacataaatg ctaattcttt tacaagggat atatcatact ttctacaaga aaatgatcaa     780
cgtaagttaa aacaaataag aaatcatttt gacaatgccg atatcgttat gtttgatgac     840
tttcaaagtt acggaatagg caataaaaaa gcaaccattg aactaatttt taatatttta     900
gacagcagga taaaccaaaa aagaaccaca ataatttgtt ccgaccggcc tatatattca     960
ttacaaaatt catttgatgc tagattgata agccgtcttt caatgggatt acaacttca     1020 attgatgaac cgcaaaaagc agacttgctg aaaatattag attatatgat taacataaac    1080
aagatgacgc ctgaactatg agaagacgac gcaaaaattt ttattgttaa gaaccatgca    1140
aacagtataa gaagtttaat tggcgctata aatcgtctaa ggttctataa ttctgaaatt    1200
gttaaaacaa attcaagata tacgcttgcc atagttaatt caattcttaa agacattcag    1260
caagtaaaag aaaaagttac gccagatgtt attattgaat acgttgctaa atactacaag    1320
ctttcgcgtt ctgaaatact aggtaaaagt agaagaaaag atgtggtttt agctagacat    1380
atagctattt gaattgttaa aaagcaatta gacttatcac tggaacaaat tgggaagttt    1440
tttggcaata gagaccactc taccattatt aatgctgtta gaaaaattga gaaagaaaca    1500
gagcaatctg atagaacatt taagagaact attttctgaaa taagcaacga gattttaag    1560
```

-continued

```
aaaagttaac attttaaaaa acatttataa acataatgtt ttctgcaaaa atgcaaaaaa    1620
acgattaaaa aaacagcaaa attaattctt tttatactta tcaacaaatt aacaaaacat    1680
atatttatta tttaaggaaa aaatgaaaat tattgtaaa                           1719

<210> SEQ ID NO 2
<211> LENGTH: 163
<212> TYPE: DNA
<213> ORGANISM: Mycoplasma bovis

<400> SEQUENCE: 2
ttaagaaaag ttaacatttt aaaaaacatt tataaacata atgttttctg caaaaatgca      60
aaaaaacgat taaaaaaaca gcaaaattaa ttctttttat acttatcaac aaattaacaa     120
aacatatatt tattatttaa ggaaaaatga aaattattgt aaa                      163

<210> SEQ ID NO 3
<211> LENGTH: 126
<212> TYPE: DNA
<213> ORGANISM: Mycoplasma bovis

<400> SEQUENCE: 3
tagcattaca ctaaaacttt tttattaaat agtaaaatgt aaatacaatg tgaaattgta      60
attaataatt acaatatggc gcattgcaca taaaatattt aaggacatat tatgagtaag    120
aaaaat                                                               126
```